(12) United States Patent
Aragane et al.

(10) Patent No.: US 8,232,447 B2
(45) Date of Patent: Jul. 31, 2012

(54) ANIMAL HAVING MODIFICATION IN MGAT2 GENE

(75) Inventors: Katsumi Aragane, Toyonaka (JP); Katsuya Ohbuchi, Tsukuba (JP); Yoshitaka Tamai, Tsukuba (JP); Naomoto Harada, Tsukuba (JP); Naomi Murai, Tsukuba (JP); Yoshiki Ito, Tsukubai (JP); Jun Kusunoki, Singapore (SG); Yukina Tokushima, Tsukuba (JP); Takaharu Maruyama, Tsukuba (JP)

(73) Assignee: MSD K.K., Tokyo (JP)

( * ) Notice: Subject to any disclaimer, the term of this patent is extended or adjusted under 35 U.S.C. 154(b) by 195 days.

(21) Appl. No.: 12/525,410

(22) PCT Filed: Nov. 30, 2007

(86) PCT No.: PCT/JP2007/073159
§ 371 (c)(1),
(2), (4) Date: Aug. 12, 2009

(87) PCT Pub. No.: WO2008/093464
PCT Pub. Date: Aug. 7, 2008

(65) Prior Publication Data
US 2010/0074888 A1    Mar. 25, 2010

(30) Foreign Application Priority Data
Jan. 31, 2007 (JP) .................. 2007-022088

(51) Int. Cl.
*A01K 67/027* (2006.01)
*A01K 67/00* (2006.01)
*C07H 21/02* (2006.01)
*C07H 21/04* (2006.01)

(52) U.S. Cl. ............. 800/18; 800/13; 800/14; 536/23.1; 536/23.7

(58) Field of Classification Search .................. 800/13, 800/14, 18; 536/23.1, 23.7
See application file for complete search history.

(56) References Cited

U.S. PATENT DOCUMENTS
2003/0161831 A1* 8/2003 Cases et al.
2006/0228762 A1* 10/2006 Marth et al.

OTHER PUBLICATIONS

Houdebine, L-M., 2002, Journal of Biotechnology, vol. 98, p. 145-160.*
Sigmund, C., Jun. 2000. Arterioscler. Thromb. Vasc. Biol., p. 1425-1429.*
Rescher et al., 2004, Journal of Cell Science, vol. 117, p. 2631-2639.*
Mogil et al., 1999, Pain, vol. 80, pp. 67-82.*
Schalkwyk et al., 2007, Genes, Brain and Behavior, vol. 6, p. 299-303.*
Cao, et al., "Properties of the Mouse Intestinal Acyl-CoA:Monoacylglycerol Acyltransferase, MGAT2", The Journal of Biological Chemistry, 2003, p. 25657-25663, vol. 278, No. 28.
Cao, et al., "A Predominant Role of Acyl-CoA:monoacylglycerol Acyltransferase-2 in Dietary Fat Absorption Implicated by Tissue Distribution, Subcellular Localization, and Up-regulation by High Fat Diet", The Journal of Biological Chemistry, 2004, p. 18878-18886, vol. 279, No. 18.
Cao, et al., "Cloning and Functional Characterization of a Mouse Intestinal Acyl-CoA:Monoacylglycerol Acyltransferase, MGAT2", The Journal of Biological Chemistry, 2003, p. 13860-13866, vol. 278, No. 16.
Coleman, et al., "Hepatic Monoacylglycerol Acyltransferase", The Journal of Biological Chemistry, 1984, p. 8934-8938, vol. 259, No. 14.
Yen, et al., "MGAT2, a Monoacylglycerol Acyltransferase Expressed in the Small Intestine", The Journal of Biological Chemistry, 2003, p. 18532-18537, vol. 278, No. 20.
Yen, et al., "The triacylglycerol synthesis enzyme DGAT1 also catalyzes the synthesis of diacylglycerols, waxes, and retinyl esters", Journal of Lipid Research, 2005, p. 1502-1511, vol. 46.
Yen, et al., "Identification of a gene encoding MGAT1, a monoacylglycerol acyltransferase", Proc. Natl. Acad. Sci, 2002, p. 8512-8517, vol. 99, No. 13.

* cited by examiner

*Primary Examiner* — Shin-Lin Chen
(74) *Attorney, Agent, or Firm* — Janet E. Fair; John C. Todaro

(57) ABSTRACT

It is an object to provide a gene-modified non-human animal having inactivated MGAT2 gene and a gene-modified non-human animal cell, which are useful for the search of the function of MGAT2 in vivo. It is another object to provide a method for screening of a compound capable of inhibiting the activity of MGAT2 and a compound capable of inhibiting the activity of MGAT2. It is further another object to provide a method for detecting a disease induced by abnormal lipid metabolism based on the expression level or activity of MGAT2. A method for screening of a compound by using a gene-modified non-human mammal having the artificially inhibited expression of MGAT2 gene and a cell thereof enable to prevent or treat a disease induced by abnormal lipid metabolism. Also a screening of a compound capable of inhibiting or enhancing the function of MGAT2 enables to prevent or treat a disease induced by abnormal lipid metabolism.

4 Claims, 3 Drawing Sheets

[Fig. 1]
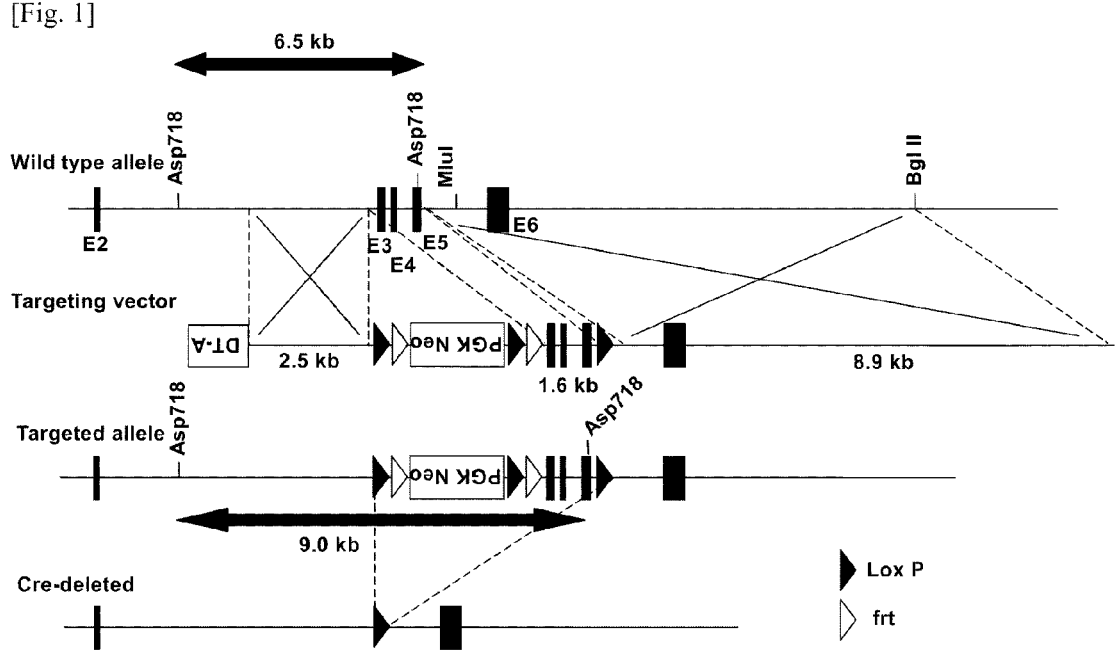
[Fig. 2]
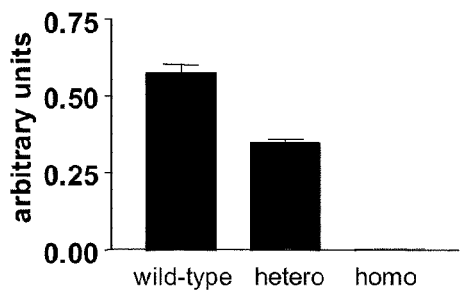
[Fig. 3]
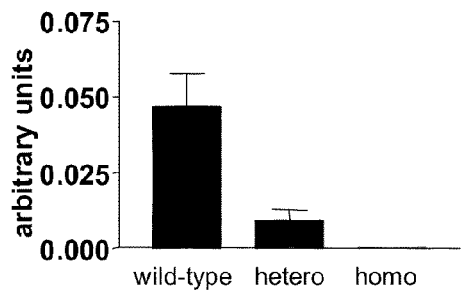

[Fig. 4]
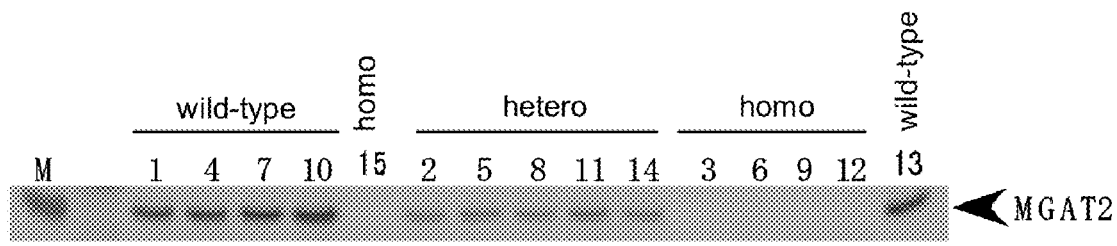
[Fig. 5]
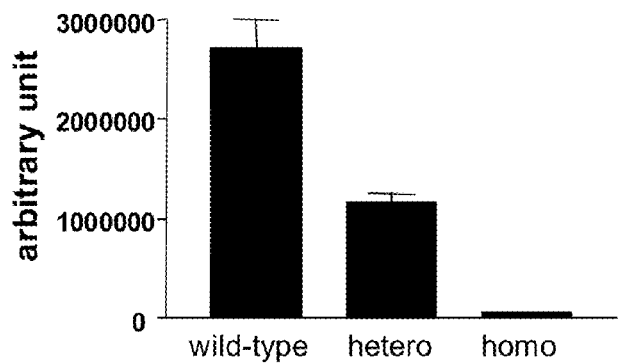
[Fig. 6]
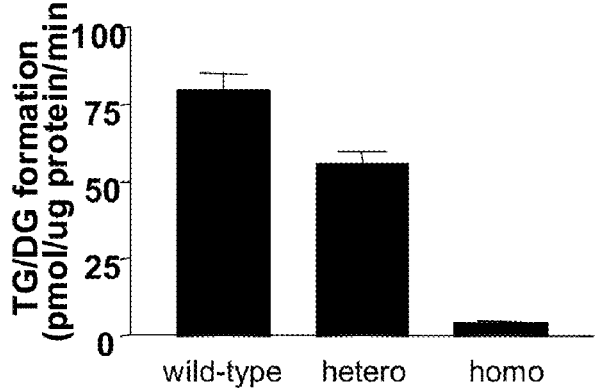

[Fig. 7]
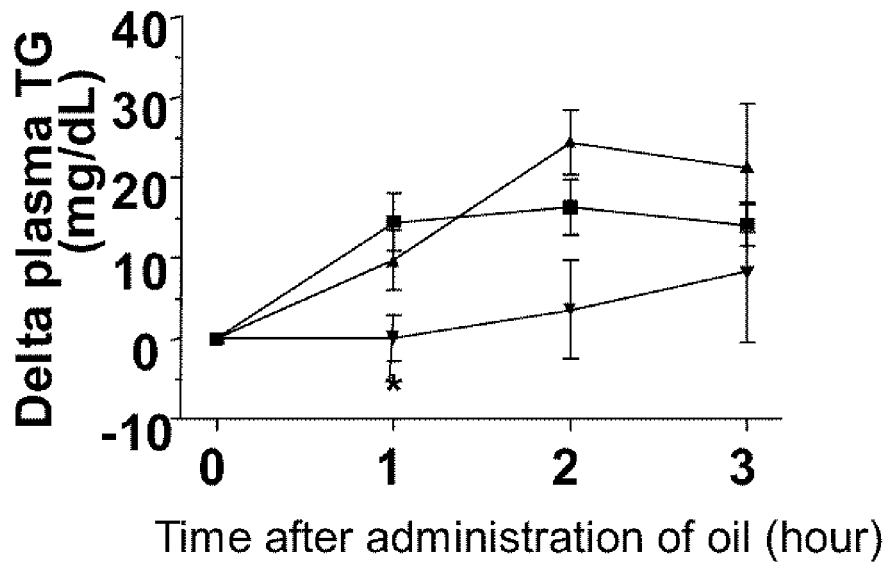
[Fig. 8]
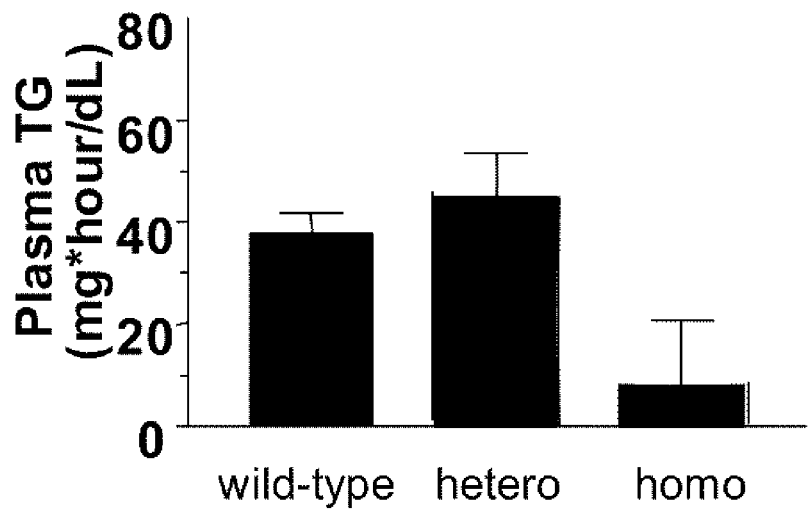

SEQUENCE LISTING

```
<160> NUMBER OF SEQ ID NOS: 14

<210> SEQ ID NO 1
<211> LENGTH: 1005
<212> TYPE: DNA
<213> ORGANISM: homo sapiens
<220> FEATURE:
<221> NAME/KEY: CDS
<222> LOCATION: (1)..(1005)
<223> OTHER INFORMATION:

<400> SEQUENCE: 1 atg gta gag ttc gcg ccc ttg ttt atg ccg tgg gag cgc agg ctg cag        48
Met Val Glu Phe Ala Pro Leu Phe Met Pro Trp Glu Arg Arg Leu Gln
1               5                   10                  15 aca ctt gct gtc cta cag ttt gtc ttc tcc ttg gca ctg gcc gag            96
Thr Leu Ala Val Leu Gln Phe Val Phe Ser Phe Leu Ala Leu Ala Glu
                20                  25                  30 atc tgc act gtg ggc ttc ata gcc ctc ctg ttt aca aga ttc tgg ctc       144
Ile Cys Thr Val Gly Phe Ile Ala Leu Leu Phe Thr Arg Phe Trp Leu
            35                  40                  45 ctc act gtc ctg tat gcg gcc tgg tgg tat ctg gac cga gac aag cca       192
Leu Thr Val Leu Tyr Ala Ala Trp Trp Tyr Leu Asp Arg Asp Lys Pro
        50                  55                  60 cgg cag ggg ggc cgg cac atc cag gcc atc agg tgc tgg act ata tgg       240
Arg Gln Gly Gly Arg His Ile Gln Ala Ile Arg Cys Trp Thr Ile Trp
65                  70                  75                  80 aag tac atg aag gac tat ttc ccc atc tcg ctg gtc aag act gct gag       288
Lys Tyr Met Lys Asp Tyr Phe Pro Ile Ser Leu Val Lys Thr Ala Glu
                85                  90                  95 ctg gac ccc tct cgg aac tac att gcg ggc ttc cac ccc cat gga gtc       336
Leu Asp Pro Ser Arg Asn Tyr Ile Ala Gly Phe His Pro His Gly Val
                100                 105                 110 ctg gca gtc gga gcc ttt gcc aac ctg tgc act gag agc aca ggc ttc       384
Leu Ala Val Gly Ala Phe Ala Asn Leu Cys Thr Glu Ser Thr Gly Phe
            115                 120                 125 tct tcg atc ttc ccc ggt atc cgc ccc cat ctg atg atg ctg acc ttg       432
Ser Ser Ile Phe Pro Gly Ile Arg Pro His Leu Met Met Leu Thr Leu
        130                 135                 140 tgg ttc cgg gcc ccc ttc ttc aga gat tac atc atg tct gca ggg ttg       480
Trp Phe Arg Ala Pro Phe Phe Arg Asp Tyr Ile Met Ser Ala Gly Leu
145                 150                 155                 160 gtc aca tca gaa aag gag agt gct gct cac att ctg aac agg aag ggt       528
Val Thr Ser Glu Lys Glu Ser Ala Ala His Ile Leu Asn Arg Lys Gly
                165                 170                 175 ggc gga aac ttg ctg ggc atc att gta ggg ggt gcc cag gag gcc ctg       576
Gly Gly Asn Leu Leu Gly Ile Ile Val Gly Gly Ala Gln Glu Ala Leu
            180                 185                 190 gat gcc agg cct gga tcc ttc acg ctg tta ctg cgg aac cga aag ggc       624
Asp Ala Arg Pro Gly Ser Phe Thr Leu Leu Leu Arg Asn Arg Lys Gly
        195                 200                 205 ttc gtc agg ctc gcc ctg aca cac ggg gca ccc ctg gtg cca atc ttc       672
Phe Val Arg Leu Ala Leu Thr His Gly Ala Pro Leu Val Pro Ile Phe
    210                 215                 220 tcc ttc ggg gag aat gac cta ttt gac cag att ccc aac tct tct ggc       720
Ser Phe Gly Glu Asn Asp Leu Phe Asp Gln Ile Pro Asn Ser Ser Gly
```

```
tcc tgg tta cgc tat atc cag aat cgg ttg cag aag atc atg ggc atc     768
Ser Trp Leu Arg Tyr Ile Gln Asn Arg Leu Gln Lys Ile Met Gly Ile
                245                 250                 255 tcc ctc cca ctc ttt cat ggc cgt ggt gtc ttc cag tac agc ttt ggt     816
Ser Leu Pro Leu Phe His Gly Arg Gly Val Phe Gln Tyr Ser Phe Gly
            260                 265                 270 tta ata ccc tac cgc cgg ccc atc acc act gtg gtg ggg aag ccc atc     864
Leu Ile Pro Tyr Arg Arg Pro Ile Thr Thr Val Val Gly Lys Pro Ile
        275                 280                 285 gag gta cag aag acg ctg cat ccc tcg gag gag gag gtg aac cag ctg     912
Glu Val Gln Lys Thr Leu His Pro Ser Glu Glu Glu Val Asn Gln Leu
    290                 295                 300 cac cag cgt tat atc aaa gag ctg tgc aac ctc ttc gag gcc cac aaa     960
His Gln Arg Tyr Ile Lys Glu Leu Cys Asn Leu Phe Glu Ala His Lys
305                 310                 315                 320 ctt aag ttc aac atc cct gct gac cag cac ttg gag ttc tgc tga        1005
Leu Lys Phe Asn Ile Pro Ala Asp Gln His Leu Glu Phe Cys
                325                 330
```

<210> SEQ ID NO 2
<211> LENGTH: 334
<212> TYPE: PRT
<213> ORGANISM: homo sapiens

<400> SEQUENCE: 2

```
Met Val Glu Phe Ala Pro Leu Phe Met Pro Trp Glu Arg Arg Leu Gln
1               5                   10                  15

Thr Leu Ala Val Leu Gln Phe Val Phe Ser Phe Leu Ala Leu Ala Glu
            20                  25                  30

Ile Cys Thr Val Gly Phe Ile Ala Leu Leu Phe Thr Arg Phe Trp Leu
        35                  40                  45

Leu Thr Val Leu Tyr Ala Ala Trp Trp Tyr Leu Asp Arg Asp Lys Pro
    50                  55                  60

Arg Gln Gly Gly Arg His Ile Gln Ala Ile Arg Cys Trp Thr Ile Trp
65                  70                  75                  80

Lys Tyr Met Lys Asp Tyr Phe Pro Ile Ser Leu Val Lys Thr Ala Glu
                85                  90                  95

Leu Asp Pro Ser Arg Asn Tyr Ile Ala Gly Phe His Pro His Gly Val
            100                 105                 110

Leu Ala Val Gly Ala Phe Ala Asn Leu Cys Thr Glu Ser Thr Gly Phe
        115                 120                 125

Ser Ser Ile Phe Pro Gly Ile Arg Pro His Leu Met Met Leu Thr Leu
130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Arg Asn Arg Lys Gly
        195                 200                 205

Phe Val Arg Leu Ala Leu Thr His Gly Ala Pro Leu Val Pro Ile Phe
    210                 215                 220

Ser Phe Gly Glu Asn Asp Leu Phe Asp Gln Ile Pro Asn Ser Ser Gly
225                 230                 235                 240

Ser Trp Leu Arg Tyr Ile Gln Asn Arg Leu Gln Lys Ile Met Gly Ile
```

```
                245                 250                 255
Ser Leu Pro Leu Phe His Gly Arg Gly Val Phe Gln Tyr Ser Phe Gly
            260                 265                 270

Leu Ile Pro Tyr Arg Arg Pro Ile Thr Thr Val Val Gly Lys Pro Ile
        275                 280                 285

Glu Val Gln Lys Thr Leu His Pro Ser Glu Glu Val Asn Gln Leu
    290                 295                 300

His Gln Arg Tyr Ile Lys Glu Leu Cys Asn Leu Phe Glu Ala His Lys
305                 310                 315                 320

Leu Lys Phe Asn Ile Pro Ala Asp Gln His Leu Glu Phe Cys
                325                 330

<210> SEQ ID NO 3
<211> LENGTH: 1728
<212> TYPE: DNA
<213> ORGANISM: Mus musculus
<220> FEATURE:
<221> NAME/KEY: CDS
<222> LOCATION: (4)..(1008)
<223> OTHER INFORMATION:

<400> SEQUENCE: 3
```

| | | | | | | | | | | | | | | | | |
|---|---|---|---|---|---|---|---|---|---|---|---|---|---|---|---|---|
| agc | atg gtg gag ttc gcc ccc ctg ttg gta cca tgg gag cgc agg cta | | | | | | | | | | | | | | | 48 |
| | Met Val Glu Phe Ala Pro Leu Leu Val Pro Trp Glu Arg Arg Leu | | | | | | | | | | | | | | | |
| | 1 | | | 5 | | | | | 10 | | | | | 15 | | |

```
cag acc ttc gcg gtc ctt cag tgg gtc ttc tcc ttc ctg gcc ttg gcc        96
Gln Thr Phe Ala Val Leu Gln Trp Val Phe Ser Phe Leu Ala Leu Ala
             20                  25                  30 cag ctc tgc atc gtc atc ttc gta ggc ctc cta ttc aca agg ttc tgg       144
Gln Leu Cys Ile Val Ile Phe Val Gly Leu Leu Phe Thr Arg Phe Trp
         35                  40                  45 ctc ttc tct gtc ctg tat gcc acc tgg tgg tac ctg gac tgg gac aag       192
Leu Phe Ser Val Leu Tyr Ala Thr Trp Trp Tyr Leu Asp Trp Asp Lys
     50                  55                  60 ccg cgg cag gga ggc cgg ccc atc cag ttc ttc aga cgc ttg gcc ata       240
Pro Arg Gln Gly Gly Arg Pro Ile Gln Phe Phe Arg Arg Leu Ala Ile
 65                  70                  75 tgg aag tac atg aag gat tat ttc cct gtc tct ttg gtc aag aca gct       288
Trp Lys Tyr Met Lys Asp Tyr Phe Pro Val Ser Leu Val Lys Thr Ala
 80                  85                  90                  95 gag ctg gac cct tcc cgg aac tac atc gcg ggc ttc cac ccc cat gga       336
Glu Leu Asp Pro Ser Arg Asn Tyr Ile Ala Gly Phe His Pro His Gly
                100                 105                 110 gtc cta gcg gct gga gcc ttt ctt aac ctg tgc act gaa agc acg ggc       384
Val Leu Ala Ala Gly Ala Phe Leu Asn Leu Cys Thr Glu Ser Thr Gly
            115                 120                 125 ttt acc tcg ctt ttc ccg ggc atc cgc tcc tat ctg atg atg ctg act       432
Phe Thr Ser Leu Phe Pro Gly Ile Arg Ser Tyr Leu Met Met Leu Thr
        130                 135                 140 gtg tgg ttc cgg gcc ccc ttc ttc cga gat tac atc atg tct ggg ggg       480
Val Trp Phe Arg Ala Pro Phe Phe Arg Asp Tyr Ile Met Ser Gly Gly
    145                 150                 155 ctg gtc tca tca gaa aag gtg agt gcc gat cac att ctg tcc agg aag       528
Leu Val Ser Ser Glu Lys Val Ser Ala Asp His Ile Leu Ser Arg Lys
160                 165                 170                 175 ggc ggc ggg aac ttg ctt gcc atc atc gtt ggg gcg cag gag gca           576
Gly Gly Gly Asn Leu Leu Ala Ile Ile Val Gly Ala Gln Glu Ala
                180                 185                 190 ctg gac gcc agg cct gga gcc tac agg ctg ctg ctg aag aat cgc aag       624
Leu Asp Ala Arg Pro Gly Ala Tyr Arg Leu Leu Leu Lys Asn Arg Lys
            195                 200                 205
```

```
ggc ttc atc agg ctc gcc ctg atg cat ggg gca gct ctt gtg cca atc      672
Gly Phe Ile Arg Leu Ala Leu Met His Gly Ala Ala Leu Val Pro Ile
        210                 215                 220 ttc tcc ttt gga gaa aac aac ctg ttc aac cag gtt gag aac acc cct      720
Phe Ser Phe Gly Glu Asn Asn Leu Phe Asn Gln Val Glu Asn Thr Pro
225                 230                 235 ggt acc tgg ctg cgc tgg atc cag aac cgg cta cag aag atc atg ggc      768
Gly Thr Trp Leu Arg Trp Ile Gln Asn Arg Leu Gln Lys Ile Met Gly
240                 245                 250                 255 atc tcc ctc cct ctc ttc cac ggc aga ggt gtc ttc cag tac agc ttt      816
Ile Ser Leu Pro Leu Phe His Gly Arg Gly Val Phe Gln Tyr Ser Phe
            260                 265                 270 ggc ctc atg ccc ttc cgc cag ccc atc acc acc ata gtg ggg aag ccc      864
Gly Leu Met Pro Phe Arg Gln Pro Ile Thr Thr Ile Val Gly Lys Pro
        275                 280                 285 atc gag gtg cag atg aca cca cag ccc tca agg gag gag gtg gac cgg      912
Ile Glu Val Gln Met Thr Pro Gln Pro Ser Arg Glu Glu Val Asp Arg
    290                 295                 300 ctt cac cag cgc tat atc aag gag ctc tgc aag ctc ttt gag gag cac      960
Leu His Gln Arg Tyr Ile Lys Glu Leu Cys Lys Leu Phe Glu Glu His
305                 310                 315 aaa ctc aag ttc aac gtc cct gag gac cag cat ctg gag ttc tgc taa     1008
Lys Leu Lys Phe Asn Val Pro Glu Asp Gln His Leu Glu Phe Cys
320                 325                 330 gtgtctccag ccggaagaca gctgcatctg agcgcctgca ggagtgtggg attaggggga   1068
cttccacagc caccagacac tcctacaaac ctagccacaa ctgccaagat ggaagagggg   1128
gcagctccta atcctgggat tgaacctgc agccaaagct ctgaggtctc cctgtccttg    1188
gcctgtctgc acatctgtag aatggggaa aagcaggcag agagaaattc ctgaggtctc    1248
ttcccacagt tgtaatgtca ttcaaacatg accaaaggac aaacagggag aaagagaaca   1308
aaactgttct tcatctaccc ttgagggaca gtgcaagaga agccagcacc ccaggcctcc   1368
ctgtgcatgc tccctgatgc tgcttcttcc ctctgaggca gagacgggga gccaagtctg   1428
ccctggcacc tactctatgt ttcttcagat tctgggtcct ctgagctatg ataccaaagg   1488
agcccagaag gcagataagg agggcagggg tcactgacta tgaccgaggg taggtctcct   1548
tcccatatcc tgagcctcag tttccccagc cttaatgacc tgggagcgcc acactgctca   1608
ccacagaggc tccaccagag agcctcttac tcatgctttc tagtgaactc cagcctctgt   1668
cttggcactg aagggcagca ctgtacatgt tacctcaata aatgaaagga gtctgtctta   1728
```

<210> SEQ ID NO 4
<211> LENGTH: 334
<212> TYPE: PRT
<213> ORGANISM: Mus musculus

<400> SEQUENCE: 4

```
Met Val Glu Phe Ala Pro Leu Leu Val Pro Trp Glu Arg Arg Leu Gln
1               5                   10                  15

Thr Phe Ala Val Leu Gln Trp Val Phe Ser Phe Leu Ala Leu Ala Gln
            20                  25                  30

Leu Cys Ile Val Ile Phe Val Gly Leu Leu Phe Thr Arg Phe Trp Leu
        35                  40                  45

Phe Ser Val Leu Tyr Ala Thr Trp Trp Tyr Leu Asp Trp Asp Lys Pro
    50                  55                  60

Arg Gln Gly Gly Arg Pro Ile Gln Phe Phe Arg Arg Leu Ala Ile Trp
65                  70                  75                  80
```

```
Lys Tyr Met Lys Asp Tyr Phe Pro Val Ser Leu Val Lys Thr Ala Glu
                 85                  90                  95

Leu Asp Pro Ser Arg Asn Tyr Ile Ala Gly Phe His Pro His Gly Val
            100                 105                 110

Leu Ala Ala Gly Ala Phe Leu Asn Leu Cys Thr Glu Ser Thr Gly Phe
        115                 120                 125

Thr Ser Leu Phe Pro Gly Ile Arg Ser Tyr Leu Met Met Leu Thr Val
    130                 135                 140

Trp Phe Arg Ala Pro Phe Arg Asp Tyr Ile Met Ser Gly Gly Leu
145                 150                 155                 160

Val Ser Ser Glu Lys Val Ser Ala Asp His Ile Leu Ser Arg Lys Gly
                165                 170                 175

Gly Gly Asn Leu Leu Ala Ile Ile Val Gly Ala Gln Glu Ala Leu
            180                 185                 190

Asp Ala Arg Pro Gly Ala Tyr Arg Leu Leu Lys Asn Arg Lys Gly
        195                 200                 205

Phe Ile Arg Leu Ala Leu Met His Gly Ala Ala Leu Val Pro Ile Phe
    210                 215                 220

Ser Phe Gly Glu Asn Asn Leu Phe Asn Gln Val Glu Asn Thr Pro Gly
225                 230                 235                 240

Thr Trp Leu Arg Trp Ile Gln Asn Arg Leu Gln Lys Ile Met Gly Ile
                245                 250                 255

Ser Leu Pro Leu Phe His Gly Arg Gly Val Phe Gln Tyr Ser Phe Gly
            260                 265                 270

Leu Met Pro Phe Arg Gln Pro Ile Thr Thr Ile Val Gly Lys Pro Ile
        275                 280                 285

Glu Val Gln Met Thr Pro Gln Pro Ser Arg Glu Val Asp Arg Leu
    290                 295                 300

His Gln Arg Tyr Ile Lys Glu Leu Cys Lys Leu Phe Glu Glu His Lys
305                 310                 315                 320

Leu Lys Phe Asn Val Pro Glu Asp Gln His Leu Glu Phe Cys
                325                 330

<210> SEQ ID NO 5
<211> LENGTH: 35
<212> TYPE: DNA
<213> ORGANISM: Artificial
<220> FEATURE:
<223> OTHER INFORMATION: synthetic polynucleotide

<400> SEQUENCE: 5
acgcgtgagg gaaagtcttt ctgaggcatc tcctc                              35

<210> SEQ ID NO 6
<211> LENGTH: 38
<212> TYPE: DNA
<213> ORGANISM: Artificial
<220> FEATURE:
<223> OTHER INFORMATION: synthetic polynucleotide

<400> SEQUENCE: 6
acgcgtccac agagatgggt gctgtgtggg acagtggg                           38

<210> SEQ ID NO 7
<211> LENGTH: 42
<212> TYPE: DNA
<213> ORGANISM: Artificial
<220> FEATURE:
<223> OTHER INFORMATION: synthetic polynucleotide
```

<400> SEQUENCE: 7
tccggaatac tcaggattat gaacatcttg agactcagag gc         42

<210> SEQ ID NO 8
<211> LENGTH: 34
<212> TYPE: DNA
<213> ORGANISM: Artificial
<220> FEATURE:
<223> OTHER INFORMATION: synthetic polynucleotide

<400> SEQUENCE: 8
tccggatctc cgctcaccta tgtggtgat gggc                   34

<210> SEQ ID NO 9
<211> LENGTH: 41
<212> TYPE: DNA
<213> ORGANISM: Artificial
<220> FEATURE:
<223> OTHER INFORMATION: synthetic polynucleotide

<400> SEQUENCE: 9
acgcgtagat ctggatcagg aatagggcct gagctagatg c           41

<210> SEQ ID NO 10
<211> LENGTH: 32
<212> TYPE: DNA
<213> ORGANISM: Artificial
<220> FEATURE:
<223> OTHER INFORMATION: synthetic polynucleotide

<400> SEQUENCE: 10
aggtagaagc agtactcggt tcacacatca cc                    32

<210> SEQ ID NO 11
<211> LENGTH: 17
<212> TYPE: DNA
<213> ORGANISM: Artificial
<220> FEATURE:
<223> OTHER INFORMATION: synthetic polynucleotide

<400> SEQUENCE: 11
ccatcaccac catagtg                                     17

<210> SEQ ID NO 12
<211> LENGTH: 16
<212> TYPE: DNA
<213> ORGANISM: Artificial
<220> FEATURE:
<223> OTHER INFORMATION: synthetic polynucleotide

<400> SEQUENCE: 12
catgcccttc cgccag                                      16

<210> SEQ ID NO 13
<211> LENGTH: 19
<212> TYPE: DNA
<213> ORGANISM: Artificial
<220> FEATURE:
<223> OTHER INFORMATION: synthetic polynucleotide

<400> SEQUENCE: 13
atctgcacct cgatgggct                                   19

<210> SEQ ID NO 14
<211> LENGTH: 15
<212> TYPE: PRT

```
-continued

<213> ORGANISM: Mus musculus

<400> SEQUENCE: 14

Ile Ile Val Gly Gly Ala Gln Glu Ala Leu Asp Ala Arg Pro Gly
1               5                   10                  15
```

ANIMAL HAVING MODIFICATION IN MGAT2 GENE

CROSS-REFERENCE TO RELATED APPLICATIONS

This application is a U.S. National Phase application under 35 U.S.C. §371 of PCT Application No. PCT/JP2007/073159, filed Nov. 30, 2007, which claims priority under 35 U.S.C. §365(b) from Japanese patent application No. JP2007-022088, filed Jan. 31, 2007.

TECHNICAL FIELD

The present invention relates to a gene-modified non-human mammal having an inactivated MGAT2 gene, a gene-modified non-human mammal cell, a method for screening a compound having a MGAT2 inhibiting effect, and a method for detecting a disease utilizing expression of MGAT2 as an indicator.

BACKGROUND ART

With the variations of dietary life in recent years, it becomes a subject of discussion that the increase of obesity, diabetes mellitus, hypertension, hyperlipemia, with the background of lack of balance in in vivo energy, is a factor leading to occurrence of arteriosclerotic disease. The arteriosclerotic disease is known to be the main cause of death as in malignant tumors. In particular, the hyperlipemia is a pathological state showing a high serum cholesterol or neutral fat (TG: triglycerid or triacylglycerol) value, which in some cases occurs hereditarily, but in many cases it depends on acquired factors such as excessive eating, hyperalimentation, shortage of exercise, etc.

In animal cells, fat is accumulated as insoluble TG in large quantities therein, and depending on need of energy it is rapidly released and decomposed, and taken out as energy necessary for action. Thus, when calorie is taken over its consumption, the excessive portion is accumulated as fat. That is, TG occurring in diet is cleaved at the ester linkages in the fatty acids present at the 1 and 3 positions of TG by lipase in digestive juice in the intestine, and further decomposed to give 2-monoacylglycerol (2-MG) and free fatty acids (FFA). These are micellized along with bile acid and absorbed into the epithelial cell of small intestine. Thus absorbed 2-MG and FFA were utilized to synthesize TG again in the cell of small intestine. There are two routes in the re-synthesis of TG in the cell of small intestine, i.e., 2-MG route and α-glycerophosphate route. Usually, 80% of TG is re-synthesized in the 2-MG route, and the remaining 20% is re-synthesized in the α-glycerophosphate route. The TG generated in the 2-MG route is utilized in the formation of chylomicron (CM) in rapid turnover, whereas the TG synthesized in the α-glycerophosphate route is once accumulated because of slow turnover in the cell of small intestine and decomposed again and sometimes utilized in the formation of CM. Thus synthesized CM is secreted into the intestinal lymph to join the blood stream (non-patent document 1).

In the synthesis of TG in the 2-MG route, an enzyme such as MGAT (Acyl-CoA: monoacylglycerol acyltransferase) or DGAT (Acyl-CoA: dinoacylglycerol acyltransferase) is specifically involved therein. MGAT catalyzes the reaction in which a diacylglycerol is produced by ligation of a fatty acyl-CoA with 2-MG produced by lipase, and DGAT catalyzes the reaction in which TG is produced by ligation of a fatty acyl-CoA with the diacylglycerol produced by the catalytic reaction of MGAT.

Although it has already been suggested that such MGAT exists in the liver and white adipocyte (non-patent document 2), the gene of MGAT1, one of the MGAT family has been cloned more recently, which was isolated from mice as a molecule highly expressed in kidney, stomach, white adipocytes and brown adipocytes (non-patent document 3). Though the activity of MGAT is noticeably observed in the small intestine, MGAT1 has not been expressed in the small intestine, and the occurrence of another molecule belonging to the MGAT family has been considered.

Thereafter, Cao et al. isolated the full length cDNA of MGAT2 from a cDNA library originating in the murine small intestine by cloning of MGAT2 by homology searching based on the cDNA sequence of MGAT1 (non-patent document 4). Mouse MGAT2 is a protein of 38.6 kDa comprising 334 amino acids, which has a signal peptide of 40 amino acids at the N-terminal and at least one transmembrane domain, and can be observed to be expressed strongly in the small intestine and kidney in addition to the weak but definite expression in the stomach, liver, skeletal muscle, and spleen (non-patent document 4). In addition, Yen at al. has reported that the human and murine MGAT2 comprises 334 amino acids and their amino acid sequence has 81% homology between human (Accession No. NM_025098; SEQ ID NO: 1) and mouse (Accession No. AY157609; SEQ ID NO: 2) based on their MGAT2 cloning (non-patent document 5).

In in vitro experiments using the Sf9 cell and COS-7 cell which have been transfected with MGAT2, it has been confirmed that the MGAT activity is enhanced in the cell membrane and MGAT2 catalyzes the acylation of rac-1-monooleoylglycerol and sn-2-monooleoylglycerol (non-patent document 5). In an experiment using the COS-7 cell in which murine MGAT2 has been expressed, it has been indicated that the MGAT2 activity is stimulated with phosphatidylcholine, phosphatidylserine and phosphatidic acid and inhibited by non-ionic and zwitter ionic surfactant, suggesting the functional difference of DGAT (non-patent document 6).

Non-patent document 1: Rinsyo Iyaku (Clinical Medicines), 21, No. 2, 216 (2005);
Non-patent document 2: J. Biol. Chem., 259, 8934 (1984);
Non-patent document 3: Proc. Natl. Acad. Sci., USA, 99, 8512 (2002);
Non-patent document 4: J. Biol. Chem., 278, 13860 (2003);
Non-patent document 5: J. Biol. Chem., 278, 18532 (2003);
Non-patent document 6: J. Biol. Chem., 278, 25657 (2003).

DISCLOSURE OF INVENTION

Problem to be Solved by the Invention

In this situation, however, there was no information on MGAT2 which type of action mechanism is involved in occurrence of its physiological function specifically in vivo, and further there was no information suggesting a direct relationship relative to physiological events or diseases caused by lipid metabolism or its aberrance. In the present circumstances, no animal model has been created for the identification of in vivo function of MGAT2.

The present invention was made in view of the problems possessed by the prior art, and the purpose of the invention is to provide a gene-modified non-human animal having an inactivated MGAT2 gene, which is useful for the research of the function of MGAT2 in vivo; and a gene-modified non-human animal cell. In addition, the invention aims to provide a method for screening a compound capable of inhibiting the MGAT2 activity and a compound capable of inhibiting the MGAT2 activity. Moreover, the invention aims to provide a method for detecting a disease induced by abnormal lipid metabolism based on the amount of expression and the activity of MGAT2.

Means for Solving the Problems

The present inventors worked assiduously to achieve the above purposes and created a gene-modified mouse in which the murine MGAT2 has been destroyed by homologous recombination, in order to elucidate the physiological role of MGAT2 in vivo. And the body weight, body fat rate, food consumption, various blood parameters, hepatic TG, and the like were measured in MGAT2-defective mice. As a result, it was found that the amount of body fat in the mice decreases compared to that in wild-type mice independently of food consumption, that the plasma TG, total cholesterol and glucose significantly decrease, and that blood free fatty acid and the amount of TG in the liver tend to decrease. Thus the invention was completed.

Namely, the gene-modified non-human mammal of the invention is characterized in that the expression of MGAT2 gene is artificially inhibited. The use of such an animal allows the evaluation and screening of a compound using MGAT2 as a target. In addition, it is also useful as a tool for analyzing the function of MGAT2 in vivo.

Further, the gene-modified non-human mammal of the invention is characterized in that an extraneous gene has been introduced into one or both of a pair of MGAT2 genes.

Further, the gene-modified non-human mammal of the invention is characterized in that the extraneous gene is a neomycin-resistant gene (neo) put between the loxP sequences or frt sequences. Such animals can be used in preparation of MGAT2-defective mice from which the neomycin-resistant gene has been removed.

In addition, the gene-modified non-human mammal of the invention is characterized in that it is a model animal of a lipid-metabolic disease.

Further, the gene-modified non-human mammal of the invention is preferably a mouse.

In addition, the gene-modified non-human mammal cell of the invention is characterized in that the expression of MGAT2 gene has been inhibited artificially. The use of such animals allows the evaluation or screening of a compound using MGAT2 as a target. In addition, it is also useful as a tool for analyzing the function of MGAT2 in vivo.

Further, the gene-modified non-human mammal cell of the invention is characterized in that an extraneous gene has been introduced into one or both of a pair of MGAT2 genes.

In addition, the invention provides a method for preparing a gene-modified non-human mammal which comprises a step in which an extraneous gene is introduced into one or both of a pair of MGAT2 genes to inactivate the expression of MGAT2 gene.

In addition, the invention provides a method for screening a compound effective in prevention or treatment of diseases induced by abnormal lipid metabolism, which comprises using any one of the above gene-modified non-human mammals or the tissues or cells derived from the mammals.

Further, as for a method for screening a compound, the invention provides a method for screening a compound effective in prevention or treatment of diseases induced by abnormal lipid metabolism, which comprises a step of administering a test compound to any one of the above gene-modified non-human mammals, a step of determining whether or not the test compound is able to function in place of MGAT2, and a step for selecting a compound capable of functioning in place of MGAT2 compared to the case of no administration of the test compound. In this screening method, a compound having an effect capable of enhancing the function of MGAT2 can be screened.

In addition, as for a method for screening (evaluating) a compound, the invention provides a method for evaluating a compound effective in prevention or treatment of a disease induced by abnormal lipid metabolism, which comprises a step of administering a test compound to any one of the above gene-modified non-human mammals and a wild-type non-human mammal, a step of analyzing the phenotypes (for example, body weight, amount of body fat, TG amount, cholesterol, glucose, free fatty acid) of the above gene-modified non-human mammal and wild-type non-human mammal, and a step for selecting a compound showing an effect capable of improving abnormal lipid metabolism only in the wild-type non-human mammal, based on comparison of the phenotypes in the gene-modified non-human mammal and in the wild-type non-human mammal. In this screening method, a compound having an effect capable of inhibiting the function of MGAT2 can be screened.

In addition, as for a method for screening a compound, the invention provides a method for screening a compound effective in prevention or treatment of diseases induced by abnormal lipid metabolism, which comprises a step of making a test compound contact with MGAT2, a step for determining the activity of MGAT2, and a step for selecting a compound capable of inhibiting or enhancing the activity of MGAT2 compared to the case of no contact with the test compound. In this screening method, a compound having an effect capable of inhibiting or enhancing the function of MGAT2 can be screened.

Further, as for a method for evaluating a compound, the invention provides a method for screening a compound effective in prevention or treatment of diseases induced by abnormal lipid metabolism, which comprises a step of making a test compound contact with a cell expressing MGAT2, a step for determining the expression level of MGAT2, and a step for selecting a test compound capable of decreasing or increasing the expression level of MGAT2 compared to the case of no contact with the test compound. In this screening method, a compound having an effect capable of inhibiting or enhancing the function of MGAT2 can be screened.

In addition, in a method for evaluating a compound, the invention provides a method for screening a compound effective in prevention or treatment of diseases induced by abnormal lipid metabolism, which comprises a step for providing a cell or cell extract containing a DNA to which a reporter gene functionally ligates at downstream of the promoter region of DNA coding for MGAT2, a step for making a test compound contact with the cell or cell extract, a step for determining the expression level of the reporter gene in the cell or cell extract, and a step for selecting a test compound capable of decreasing or increasing the expression level of the reporter gene compared to the case of no contact with the test compound. In this screening method, a compound having an effect capable of inhibiting or enhancing the function of MGAT2 can be screened.

Further, the invention provides a pharmaceutical preparation for treatment or prevention of diseases induced by abnormal lipid metabolism, which comprises as an active ingredient a compound capable of decreasing the expression or activity of MGAT2. In this situation, the compound may be selected by any one of the above screening methods.

In addition, the invention also provides a pharmaceutical preparation for treatment or prevention of diseases induced by abnormal lipid metabolism, which comprises as an active ingredient a compound capable of increasing the expression or activity of MGAT2.

Further the invention provides a method for detecting a disease induced by abnormal lipid metabolism, which comprises a step for determining the amount of the expressed MGAT2 gene of the invention.

In addition, the invention provides a method for detecting a disease induced by abnormal lipid metabolism, which comprises a step for detecting mutation in the MGAT2 gene.

Effect of the Invention

The present inventors prepared MGAT2-knock-out mice in order to elucidate the function of MGAT2 in vivo. As a result, it was clarified that MGAT2 catalyzing the synthetic reaction of TG works to control body weight, the amount of body fat, plasma TG, total cholesterol, glucose, blood free fatty acid and the amount of TG in the liver. Namely, the relationship between MGAT2 and diseases caused by aberrant metabolism of lipid relative to the synthetic route for TG was elucidated.

From these findings, the invention provides a gene-modified non-human mammal in which the expression of MGAT2 is inhibited artificially. In addition, the gene-modified non-human mammal of the invention is useful as a model animal for a disease caused by aberrance of the adipose-metabolic route, particularly synthetic route for TG, and can also be used in screening of pharmaceuticals for prevention or treatment of the disease. Further, from the above findings, it was elucidated that an MGAT2 inhibitor is effective for a disease caused by abnormal lipid metabolism. Namely, the invention also provides a method for screening a MGAT2 inhibitor using as an indicator of the activity or expression of MGAT2.

BEST MODE FOR CARRYING OUT THE INVENTION

The followings explain preferred modes for carrying out the invention in detail.

MGAT2

The MGAT2 gene of the invention (the protein coded by the relevant gene is referred to as "MGAT2") has been known in human (Accession No. NM_025098; SEQ ID NO: 1 and 2) and mouse (Accession No. AY157609; SEQ ID NO: 3 and 4).

In addition, the MGAT2 of the invention is not limited to the above examples, and includes proteins functionally equivalent to the MGAT2. The functionally equivalent protein includes proteins having the amino acid sequence of natural MGAT2, in which 1 or 2 or more amino acids are substituted, deleted, added and/or inserted. In order to prepare a DNA encoding a variant protein functionally equivalent to MGAT2 of the invention, as another method well-known to a person skilled in the art, a technique of hybridization under a stringent condition or polymerase chain reaction (PCR) can be utilized.

In the invention, the stringent condition for hybridization means those comprising 6M urea, 0.4% SDS and 0.5×SSC, or an equivalent hybridization condition for stringency. Under a condition for higher stringency, for example, a condition comprising 6M urea, 0.4% SDS and 0.1×SSC, it is expected that a DNA having higher homology can be isolated. The high homology means that the total amino acid sequence has at least 55% sequence identity, preferably 70% or more, more preferably 90% or more, particularly preferably 95% or more sequence identity. In this connection, the variable amino acid number in the mutant is usually within 30 amino acids, preferably 15 amino acids or less, more preferably 5 amino acids or less, even more preferably 3 amino acids or less, particularly preferably 2 amino acids or less. In this situation, the sequence identity of amino acids or bases can be determined by using the algorithm BLAST by Karlin and Altschul (Proc. Natl. Acad. Sci. USA, 87, 2264 (1990); Proc. Natl. Acad. Sci. USA, 90, 5873 (1993)). Another program called as BLASTN or BLASTX based on the algorithm BLAST has been developed (J. Mol/Biol., 215, 403 (1990)); in analyzing a base sequence with BLASTN, the parameter is assumed to be, for example, score=100 and wordlength=3. In analyzing an amino acid sequence with BLASTX, the parameter is assumed to be, for example, score=50 and wordlength=3.

The animal species used in the invention, from which MGAT2 is derived, includes, but not limited to, human, mouse, rat, monkey, guinea pig, swine, and ferret.

Gene-Modified Non-Human Mammals and Gene-Modified Non-Human Animal Cells

The gene-modified non-human mammal of the invention is characterized in that the expression of MGAT2 gene is inhibited artificially.

In the invention, the phrase "the expression of MGAT2 gene is inhibited artificially" usually indicates a state in which the expression of gene is inhibited by mutation of the gene such as insertion, deletion, substitution, etc. of a nucleotide or nucleotides in one or both of a pair of MGAT2 genes. When a mutated MGAT2 protein in which the normal function as the MGAT2 protein is decreased or lost is expressed, such a state is also included in the phrase "the expression of the MGAT2 gene is inhibited". The above "inhibition" includes also the complete inhibition of the expression of MGAT2 gene as well as the inhibition of the expression of only one of the gene pair. The site of gene mutation in the invention may be located anywhere as far as the expression of MGAT2 gene is inhibited, including exon site, promoter site, and the like.

The animal species intended for the improvement of MGAT2 gene usually includes mammals other than human, preferably rodent such as mouse, rat, guinea pig, rabbit, swine; particularly mouse is preferred above all.

In addition, the invention provides a gene-modified mammal cell in which the expression of MGAT2 gene is inhibited artificially. Such a cell is useful as a model cell for diseases caused by abnormal lipid metabolism. In the invention, there is no particular limitation in the animal species from which the cell intended for the improvement of MGAT2 gene is derived, and the cells derived from a variety of animal species including human are involved. The sort of the cell intended for the improvement of MGAT2 gene in the invention includes, for example, but not limited to, somatic cell, fertilized ovum, ES cell, and the cell established from the gene-modified non-human mammal of the invention. In the invention, the cell strain derived from the gene-modified non-human mammal may be established according to a well-known method; for example, a method of primary culture of fetal cells for rodents may be utilized.

In the gene-modified non-human mammals and the gene-modified non-human mammal cells of the invention, in order to artificially inhibit the expression of MGAT2 gene, although a method for deleting all or part of the MGAT2 gene or a method for deleting all or part of the expression-controlling region of the MGAT2 gene may be employed, preferably a method for inactivating the MGAT2 gene by inserting an exogenous gene into one or both of a pair of MGAT2 genes is employed. Namely, in a preferred embodiment of the invention, the gene-modified non-human mammal and the gene-modified non-human mammal cell are characterized in that an exogenous gene has been inserted into one or both of a pair of MGAT2 genes.

The gene-modified non-human mammal of the invention can be prepared by means of a gene engineering technology well known to a person skilled in the art. For example, the gene-modified mouse can be prepared as follows. First, a DNA containing the exon portion of MGAT2 gene is isolated from mice, and all or part of the MGAT2 gene sequence is deleted, or subjected to insertion of or substitution with another gene according to a gene engineering technology. In general, a proper marker gene is inserted into all or part of the MGAT2 gene sequence to construct a targeting vector. The marker gene to be inserted preferably includes antibiotic resistant genes such as neomycin resistant gene or hygromycin resistant gene; and reporter genes such as β-galactosidase gene (lacZ), chloramphenicol acetyl-transferase gene (cat), luciferase gene or GFP (green fluorescent protein) gene. When an antibiotic resistant gene is inserted, the resulting cell strain with homologous recombination can be screened by merely culturing on a medium containing the antibiotic. In addition, in order to screen efficiently, it is possible to make a thymidine kinase gene bind to the targeting vector. Thus, the cell strain in which non-homologous recombination occurs can be eliminated. When a reporter gene is inserted to destroy the function of exon, the reporter gene is preferably inserted so as to be expressed under control of the promoter of MGAT2. The vector which is used in preparation of a targeting vector includes, for example, pBR322, pBR325, pUC12, pUB110, pTB5, pSH19, pSH15, and pKO.

It is also possible to utilize a system for inducing gene recombination within cells. Such a system includes, for example, Cre-loxP system, and FLP-FRT system. The Cre-loxP system is composed of a DNA comprising a certain base sequence termed loxP and an enzyme termed Cre recombinase which recognizes the loxP sequence to recombine genes. Cre is a recombinase obtained from bacteriophage P1, allowing the construction of the system, that is, the loxP sequences are introduced into the targeting vector so that the desired region is put between two loxP sequences; thus, the region put between the loxP sequences can be cut off with the Cre recombinase enzyme. For example, the above marker gene or reporter gene is structurally put between the two loxP sequences to prepare a targeting vector, which is used in preparation of a gene-modified animal. Thus prepared animal is mated with a mouse which has expressed Cre recombinase, where Cre recognizes the loxP sequence to recombine DNAs. As a result, the loxP sequences conjugate each other to yield a gene-modified animal, in which the marker gene or reporter gene put between the loxP sequences has been eliminated.

The transgenic animal capable of expressing Cre recombinase may be prepared according to a well-known method; for example, an expression vector in which the Cre recombinase gene (Accession No. X03453) has been placed in the downstream of a suitable expression control region, is introduced into a germinal cell such as unfertilized egg, fertilized egg, sperm and progenitor cell thereof, incubated nearly overnight, and transplanted to the oviduct of a surrogate mother to yield a transgenic chimera animal. The resulting transgenic chimera animal is mated with a normal animal, after confirmation by analysis of the somatic gene that the vector construct is integrated into the genome. The F1 animal obtained by mating is a transgenic animal of heterozygote, which can be crossed with F1 to yield a Cre transgenic animal of homozygote.

Thus resulting animal having a gene-modified site, from which the marker gene or reporter gene has been eliminated by the Cre-loxP system and the like, shows no phenotype which could be generated due to the existence of the marker gene or reporter gene, and therefore it allows a phenotypic analysis focused on MGAT2 alone as an object of analysis.

Thus resulting targeting vector is introduced into an ES cell strain of a mouse and the like by means of electroporation etc. to screen the cell strain yielding homologous recombination. Specifically, the targeting vector is introduced into a non-human mammal ES cell or non-human animal egg cell according to a well-known method (electroporation method, microinjection method, calcium phosphate method, lipofection method, particle gun method, etc.), and the inactivated MGAT2 gene sequence contained in the targeting vector is replaced by the MGAT2 gene on the chromosome of non-human mammal ES cell or non-human animal egg cell by homologous recombination for screening.

The cell in which the MGAT2 gene has been knocked out can be determined by means of a Southern hybridization analysis using as a probe a DNA sequence on the MGAT2 gene or proximal region thereof or by means of a PCR analysis using as a primer a DNA sequence of the targeting vector or of the region proximal to the MGAT2 gene.

When a non-human animal ES cell is used, a cell strain in which the MGAT2 gene has been inactivated is cloned by homologous recombination, and the resulting cell is injected into the non-human animal embryo or blastocyst at an early proper phase of embryogenesis, e.g. the 8th cell phase, or the ES cell cluster is put between 2 embryos of the 8th cell phase in which the MGAT2 gene has been inactivated, to yield a chimera embryo, which is transplanted to the uterus of a pseudopregnant non-human animal.

Thus prepared animal is a chimera animal which is constituted by both of cells having the normal MGAT2 gene locus and cells having the artificially mutated MGAT2 gene locus. When a part of the germ cells of this chimera animal has the mutated MGAT2 gene locus, an individual in which all of the tissues are constituted by the cells having the artificially mutated MGAT2 gene locus can be obtained from a population obtained by mating a chimera individual with a normal individual by screening, for example, according to the coat color determination. Thus resulting individuals are generally in failure of the MGAT2 heterogeneous expression; thus, the individuals in failure of the MGAT2 heterogeneous expression are mated each other, and individuals in failure of the MGAT2 homogeneous expression can be obtained from their progeny.

When egg cells are used, for example, transgenic non-human animals in which a targeting vector is introduced into the chromosome can be obtained by injecting a gene solution into the nucleus of egg cell by a microinjection method; these transgenic non-human animals are compared and those in which the MGAT2 gene locus has been mutated by homologous recombination can be chosen.

For the non-human animals in failure of the MGAT2 gene expression, the amount of mRNA of MGAT2 in the animals is determined according to a well-known method to compare indirectly the amount of expression; thus, these animals can be distinguished from normal animals.

The individuals in which the MGAT2 gene has been knocked out can be bred and passaged in a conventional breeding environment, after confirmation that the MGAT2 gene of the animal individuals obtained by mating has also been knocked out. The accession and maintenance of the germ cell line may be carried out according to a well-known method. Namely, the homozygous animals having an inactivated gene sequence in both of the homologous chromosomes can be obtained by mating male and female animals keeping an MGAT2 inactivated gene sequence. The homozygous and heterozygous animals having the MGAT2 inactivated gene sequence can be bred and passaged by mating male and female heterozygous animals. The progeny of the resulting animals having the MGAT2 inactivated gene sequence is included in the non-human animals in failure of the MGAT2 gene expression of the invention.

In the gene-modified non-human mammals in which the expression of MGAT2 gene has been inhibited, the following phenotypes are observed: reduction of body weight and fat rate, and decrease of plasma TG, cholesterol, glucose amount, blood free fatty acid and liver TG. These are parameters relative to lipid metabolism, and the gene-modified non-human mammals show an improved condition of the so-called metabolic syndromes such as hyperlipemia, diabetes mellitus, and obesity. Among lipoproteins (chylomicron), very low density lipoprotein (VLDL), low density lipoprotein (LDL), and high density lipoprotein (HDL) which are formed from cholesterol/neutral fats or phospholipids linking to apoproteins in blood, when LDL cholesterol shows 140 mg/dl or more, HDL cholesterol less than 40 mg/dl, and total cholesterol (TC) 220 mg/dl or more, TG 150 mg/dl or more, then it is diagnosed to be hyperlipemia. It is known that hyperlipemia is a major cause of arteriosclerosis, which results in ischemic heart diseases (angina pectoris, myocardial infarction), stroke (cerebral hemorrhage, cerebral infarction), renal dysfunction (renal arteriosclerosis, renal failure), aberrant eye grounds (hemorrhage of the eye grounds, blindness), circulation disorder in limb (intermittent claudication, gangrene), and the like. Namely, the use of the gene-modified non-human mammals of the invention enables to evaluate or screen the compounds effective in prevention or treatment of diseases caused by abnormal lipid metabolism including the above diseases.

On the other hand, since the gene-modified non-human mammals of the invention show physiological states as mentioned above, they are useful as model animals for hypolipemia. Among four lipids, i.e., cholesterol, triglyceride, phospholipids and free fatty acids existing in blood, when any one of them is lower than normal values, it is diagnosed to be hypolipemia. The causative disease for hypolipemia includes, for example, an(hypo)β-lipoproteinemia, apoprotein B aberration, Anderson's disease, Tangier's disease, apo A-I deficiency (mutant), chronic hepatitis, hyperthyroidism, liver cirrhosis, hemolytic anemia, chronic pancreatitis, leukemia, malabsorption syndrome, malignant lymphoma, Addison's disease, chronic (acute) inflammation, malignant tumor, spleen tumor, infection, obesity, type 2 diabetes mellitus, chronic hepatitis, myeloproliferative disease, renal failure, malignant tumor, low nutrition, nephrotic syndrome, malabsorption syndrome, and the like. Namely, the use of the gene-modified non-human mammals of the invention enables to evaluate or screen the compounds effective in prevention or treatment of diseases which show a state of decrease in blood lipid caused by abnormal lipid metabolism including the above diseases, or diseases caused by such a state.

Screening of Compounds with the Gene-Modified Non-Human Mammal (Cell)

The invention provides a method for screening a compound effective in prevention or treatment of a disease induced by abnormal lipid metabolism, which comprises using a gene-modified non-human mammal in which the expression of MGAT2 gene has been inhibited artificially or using the tissues or cells derived from the mammal.

As for the gene-modified non-human mammal used in the screening method, there is no particular limitation in the way of inhibiting MGAT2; for example, the mammal in which a MGAT2 gene is inactivated by introduction of a reporter gene which is expressed under the control of a promoter for MGAT2 gene can be used. The reporter gene includes, for example, β-galactosidase gene (lacZ), chloramphenicol acetyltransferase gene (cat), luciferase gene or GFP (green fluorescent protein) gene.

The gene-modified non-human mammal in which the MGAT2 gene has been substituted by a reporter gene, since the reporter gene is placed under the control of a promoter for MGAT2, enables to detect the activity of promoter by tracing the expression of a substance coded by the reporter gene. For example, when a part of the MGAT2 gene region is substituted with lacZ, β-galactosidase is expressed in place of MGAT2 in the tissue in which MGAT2 should be expressed primarily. Thus, the in vivo expression of MGAT2 can be observed, for example, by using a reagent acting as a substrate for β-galactosidase, such as X-gal to stain. Specifically, a mouse lacking the MGAT2 gene or tissue segment thereof is fixed with glutaraldehyde etc., washed with a phosphate buffer (PBS), then allowed to react with a staining solution containing X-gal at about 37° C. for 30-60 minutes; subsequently, the tissue sample is washed with 1 mM EDTA/PBS solution to terminate the β-galactosidase reaction, and the coloration may be observed.

In the screening method, for example, a test compound is administered to a gene-modified non-human mammal; and when the expression of the reporter protein is increased, the test compound may be selected as a substance enhancing the promoter activity of MGAT2 gene. On the other hand, when the expression of the reporter protein is decreased, the test compound may be selected as a substance inhibiting the promoter activity of MGAT2 gene. The substance enhancing or inhibiting the promoter activity of MGAT2 gene, since it can modulate the expression of MGAT2, can be used as a prophylactic or therapeutic agent for diseases induced by abnormal lipid metabolism in which MGAT2 is involved, for example, obesity, hyperlipemia (hypercholesterolemia, high LDL cholesterolemia, low HDL cholesterolemia, hypertriglyceridemia), hyperinsulinemia, arteriosclerosis, ischemic heart diseases (angina pectoris, myocardial infarction), stroke (cerebral hemorrhage, cerebral infarction), renal dysfunction (renal arteriosclerosis, renal failure), aberrant eye grounds (hemorrhage of the eye grounds, blindness), circulation disorder in limb (intermittent claudication, gangrene), an(hypo) β-lipoproteinemia, apoprotein B aberration, Anderson's disease, Tangier's disease, apo A-I deficiency (mutant), chronic hepatitis, hyperthyroidism, liver cirrhosis, hemolytic anemia, chronic pancreatitis, leukemia, malabsorption syndrome, malignant lymphoma, Addison's disease, chronic (acute) inflammation, malignant tumor, spleen tumor, infection, obesity, type 2 diabetes mellitus, chronic hepatitis, myeloproliferative disease, renal failure, malignant tumor, low nutrition, nephrotic syndrome, malabsorption syndrome, and the like.

In the second embodiment of the method for screening a compound effective in prevention or treatment of a disease induced by abnormal lipid metabolism in the invention, the method comprises a step of administering a test compound to a gene-modified non-human mammal in which the expression of MGAT2 gene is inhibited artificially, a step of determining whether or not the test compound is able to function in place of MGAT2, and a step for selecting a compound capable of functioning in place of MGAT2 compared to the case of no administration of the test compound.

In the second embodiment, first a test compound is administered to the gene-modified non-human mammal of the invention. Administration to the gene-modified non-human mammal of the invention may be achieved, for example, but not limited to, orally or parenterally such as percutaneously. When the test compound is protein, for example, a viral vector having a gene coding for the protein can be constructed to introduce the gene into the gene-modified non-human mammal of the invention utilizing its infective ability.

In the second embodiment, subsequently, it is determined whether or not the test compound functions in place of MGAT2, and a compound which functions in place of MGAT2 is selected in comparison with the case of no administration of the test compound.

For example, in the case as shown below, it is determined that the test compound functions in place of MGAT2. Namely, the body weight, body fat rate, food consumption, various blood parameters (plasma glucose, plasma TG, total cholesterol), hepatic TG, or free fatty acid are measured in the gene-modified non-human mammal of the invention to which is administered a test compound and in the animal to which no test compound is administered; when the measured values are increased by administration of the test compound, it is determined that the test compound functions in place of MGAT2. Such a compound can be used as an agent for enhancing the function of MGAT2; the compound is effective in prevention or treatment of diseases caused by the decrease of lipid, for example, diseases causing hypolipemia, including, for example, an(hypo)β-lipoproteinemia, apoprotein B aberration, Anderson's disease, Tangier's disease, apo A-I deficiency (mutant), chronic hepatitis, hyperthyroidism, liver cirrhosis, hemolytic anemia, chronic pancreatitis, leukemia, malabsorption syndrome, malignant lymphoma, Addison's disease, chronic (acute) inflammation, malignant tumor, spleen tumor, infection, obesity, type 2 diabetes mellitus, chronic hepatitis, myeloproliferative disease, renal failure, malignant tumor, low nutrition, nephrotic syndrome, malabsorption syndrome, and the like.

In the third embodiment of a method for screening (evaluating) a compound effective in prevention or treatment of diseases induced by abnormal lipid metabolism, the invention provides a method for evaluating a compound effective in prevention or treatment of diseases induced by abnormal lipid metabolism, which comprises a step of administering a test compound to any one of the above gene-modified non-human mammals and to a wild-type non-human mammal, a step of analyzing the phenotypes (e.g., body weight, body fat amount, TG amount, cholesterol, glucose, free fatty acid) in the gene-modified non-human mammal and in the wild-type non-human mammal, and comparing the phenotype in the gene-modified non-human mammal with that in the wild-type non-human mammal to select the compound which shows an effect improving the abnormal lipid metabolism only in the wild-type non-human mammal.

In the third embodiment, first a test compound is administered to the gene-modified non-human mammal and to the wild-type non-human mammal Administration to the gene-modified non-human mammal and to the wild-type non-human mammal may be achieved, for example, but not limited to, orally or parenterally such as percutaneously. When the test compound is protein, for example, a viral vector having a gene coding for the protein can be constructed to introduce the gene into the gene-modified non-human mammal of the invention utilizing its infective ability.

In the third embodiment, subsequently, the phenotypes (e.g., body weight, body fat amount, TG amount, cholesterol, glucose, free fatty acid) in the gene-modified non-human mammal and in the wild-type non-human mammal are analyzed. In analysis of the phenotype, a properly preferred means can be employed according to the phenotype of the object to be analyzed; for example, when the blood TG, cholesterol, glucose, and free fatty acid are determined, the blood after collection can be measured by means of commercially available kits for each parameter. When the phenotype of the object to be analyzed is the amount of body fat, the body fat rate can be determined by means of NMR and calculated.

Subsequently, the phenotype in the gene-modified non-human mammal is compared with that in the wild-type non-human mammal, and the compound which shows an effect improving the abnormal lipid metabolism only in the wild-type non-human mammal is selected.

For example, when the decrease of body weight, decrease of body fat amount, decrease of TG amount, decrease of cholesterol value, decrease of glucose value, and decrease of free fatty acid are observed, the test compound is judged to show an effect improving abnormal lipid metabolism. Contrarily, when no change in these values is observed in the MGAT2 gene-modified non-human mammal, the test compound can be evaluated to function as a MGAT2 inhibitor. On the other hand, for example, when the increase of body weight, increase of body fat amount, increase of TG amount, increase of cholesterol value, increase of glucose value, and increase of free fatty acid are observed in the wild-type non-human mammal and no change in these values is observed in the MGAT2 gene-modified non-human mammal to which the same test compound has been administered, the test compound can be evaluated to function as a MGAT2 enhancer.

Such a screening method enables to screen a compound having an effect inhibiting or enhancing the function of MGAT2. For example, when there is a certain compound which is known effective to metabolic diseases but not clear on the action mechanism in vivo, this compound can be evaluated as a test compound by the screening method of the invention; as a result, when this has an improving action for metabolic diseases in the wild-type non-human mammal but does not show any phenotype in the MGAT2 gene-modified non-human mammal, this test compound can be evaluated to act on MGAT2 as a target.

In the third embodiment, it becomes possible to screen a compound resulting in prophylactic or therapeutic agent for diseases induced by abnormal lipid metabolism in which MGAT2 is involved, for example, obesity, hyperlipemia (hypercholesterolemia, high LDL cholesterolemia, low HDL cholesterolemia, hypertriglyceridemia), hyperinsulinemia, arteriosclerosis, ischemic heart diseases (angina pectoris, myocardial infarction), stroke (cerebral hemorrhage, cerebral infarction), renal dysfunction (renal arteriosclerosis, renal failure), aberrant eye grounds (hemorrhage of the eye grounds, blindness), circulation disorder in limb (intermittent claudication, gangrene), an(hypo)β-lipoproteinemia, apoprotein B aberration, Anderson's disease, Tangier's disease, apo A-I deficiency (mutant), chronic hepatitis, hyperthyroidism, liver cirrhosis, hemolytic anemia, chronic pancreatitis, leukemia, malabsorption syndrome, malignant lymphoma, Addison's disease, chronic (acute) inflammation, malignant tumor, spleen tumor, infection, obesity, type 2 diabetes mellitus, chronic hepatitis, myeloproliferative disease, renal failure, malignant tumor, low nutrition, nephrotic syndrome, malabsorption syndrome, and the like.

Method for Screening of Compounds

In the first embodiment of the method for screening of compounds, the invention provides a method for screening a compound effective in prevention or treatment of diseases induced by abnormal lipid metabolism, which comprises a step of making a test compound contact with MGAT2, a step for determining the MGAT2 activity, and a step for selecting a test compound capable of inhibiting the MGAT2 activity compared to the case of no administration of the test compound.

In the method for screening of compounds of the invention, first a test compound is allowed to contact with MGAT2. There is no particular limitation in the state of MGAT2 used in the first embodiment; for example, it may be in a purified state, in a state expressed in cells, or in a state expressed in a cell extract.

MGAT2 may be purified according to a well-known method. The cell expressing MGAT2 includes cells expressing intrinsic MGAT2 or cells expressing extraneous MGAT2. The cell expressing intrinsic MGAT2 includes, but not limited to, cultured cells. There is no particular limitation in the cultured cells, for example, commercially available ones may be employed. The animal species from which the cell expressing intrinsic MGAT2 is derived includes human, mouse, rat, monkey, guinea pig, ferret, and the like. The cell expressing extraneous MGAT2 may be prepared, for example, by introducing a vector containing a DNA coding for MGAT2 into a cell. The vector may be introduced into the cell according to a conventional manner, for example, calcium phosphate method, electroporation method, lipofetamine method, or microinjection method.

The cell extract in which MGAT2 is expressed includes those prepared, for example, by adding a vector containing a DNA coding for MGAT2 to a cell extract contained in a in vitro transcription/translation system. There is no particular limitation in the in vitro transcription/translation system, and a commercially available in vitro transcription/translation kit may be used.

In the screening method of the invention, the "test compound" relating to the invention includes, for example, single compound such as naturally occurring compounds, organic compounds, inorganic compounds, proteins, antibodies, peptides, nucleic acids as well as compound library, expression products of gene library, cell extracts, supernatant of cell culture, products of fermented microorganisms, extracts of marine organisms, plant extracts, procaryotic cell extracts, eucaryotic single cell extracts, or animal cell extracts. The test compound if required may properly be labeled. The label includes, for example, radiation label, fluorescence label, and the like.

In the invention, the "contact" is carried out depending on the state of MGAT2. For example, MGAT2 in a purified state may be allowed to contact by adding a test compound to the purified sample. In addition, when MGAT2 is in the expressed state in cell or in the expressed state in the cell extract, it may be allowed to contact by adding a test compound to the cell culture broth or cell extract. When the test compound is protein, for example, a vector containing a DNA coding for the protein is introduced into the cell in which MGAT2 is expressed, or the vector is added to the cell extract in which MGAT2 is expressed; thus, MGAT2 can be contacted to the test compound. Further, a two-hybrid method using yeast or animal cell may be used.

In the first embodiment, subsequently, the activity of MGAT2 is measured. The activity of MGAT2 includes that of monoacylglycerol acyltransferase (the activity producing diacylglycerol) using monoacylglycerol as a substrate. Specifically, for example, the reaction may be started to add a test compound to a solution containing a microsome fraction, 5 mM $MgCl_2$, 1 mg/ml BSA, 200 mM sucrose, 100 mM Tris-HCl (pH 7.5), 200 μM monooleic/1000 μM phosphatidylcholine, and 25 μM [$^{14}C$]-oleoyl-CoA; the reaction, however, is not limited to this condition, and for example, can be carried out according to the condition as described in Proc. Natl. Acad. Sci. USA, 99, 8512 (2002). In this connection, a monoacylglycerol is included as acyl acceptor, and fatty acyl-CoA as acyl donor. The reaction is carried out, for example, at 30-37° C. for 5-15 minutes, and terminated with addition of chloroform/methanol (2:1 by volume). The detection and determination of the activity of MGAT2 may be carried out, for example, using a $^{14}C$-labeled oleoyl-CoA as an acyl donor by detecting diacylglycerol having $^{14}C$ incorporated in the monoacyl glycerol.

Thus determined MGAT2 activity is compared with the MGAT2 activity determined in the same manner in the absence of the test compound, and the compound capable of inhibiting or enhancing the MGAT2 activity is isolated as an inhibitor or enhancer for MGAT2. Such an inhibitor has an effect inhibiting the expression or activity of MGAT2, and enables to inhibit the synthesis of TG, i.e. inhibition of the synthesis/accumulation of fat; thus, it allows to obtain a compound effective in prevention or treatment of diseases caused by the excessive synthesis and accumulation of fat. On the other hand, the compound which has been elucidated to enhance the MGAT2 activity as a result of comparison may be isolated as an MGAT2 enhancer. Such an enhancer has an effect enhancing the expression or activity of MGAT2, and enables to normalize the lack and deficiency of the synthesized TG, i.e. synthetic insufficiency of fat; it allows to obtain a compound effective in prevention or treatment of diseases caused by the synthetic insufficiency of fat.

In the second embodiment of the screening method for compounds, the invention provides a method for screening a compound effective in prevention or treatment of diseases induced by abnormal lipid metabolism, which comprises a step of making a test compound contact with an MGAT2-expressing cell, a step for determining the expression level of MGAT2, and a step for selecting a test compound capable of decreasing or increasing the expression level of MGAT2 compared to the case of no contact with the test compound.

In the second embodiment, first a cell expressing MGAT2 is allowed to contact with a test compound.

The cell expressing MGAT2 may be prepared as follows. Namely, the cell into which the MGAT gene is introduced to express MGAT2 protein may be prepared according to a method well-known to a person skilled in the art; for example, a nucleic acid comprising the MGAT2 gene or a part of thereof is cloned into an expression vector containing a preferred promoter and a transcription-controlling element, and the cloned vector containing the nucleic acid is introduced into a host cell to yield the objective cell. In this connection, there is no particular limitation in the vector to be used, as far as it can be utilized as an expression vector, including, for example, pCMV-Tag, pcDNA3.1, pBlueBacHis2, pCI-neo, pcDNAI, pMClneo, pXT1, pSG5, pEF1/V5-HisB, pCR2.1, pET11, λgt11 or pCR3.1.

Subsequently, the expression vector into which has been introduced a nucleic acid comprising the MGAT2 gene or a part of thereof is introduced in a host cell. There is no particular limitation in the host cell to be used, as far as it can be utilized usually as a cell for expression of genes, including animal cells, insect cells, plant cells, microorganisms, for example, SW480, DLD-1, CCD-18Co, CCD-841CoN, COS1, COS7, CHO, NIH/3T3, 293, Raji, CV11, C1271, MRC-5, CPAE, HeLa, 293T or Sf9. There is no particular limitation in the method for introducing an expression vector into a host cell as far as it is well known in the art, including, for example, electroporation, calcium phosphate method, DEAE-dextran method or lipofection.

In the invention, the "contact" is carried out as follows. When used in the expressed state in cell or in the expressed state in the cell extract, it may be allowed to contact by adding a test compound to the cell culture broth or cell extract, respectively. When the test compound is protein, for example, a vector containing a DNA coding for the protein is introduced into the cell in which MGAT2 is expressed, or the vector is added to the cell extract in which MGAT2 is expressed; thus, MGAT2 can be contacted to the test compound. Further, for example, a two-hybrid method using yeast or animal cell may be used.

In the second embodiment, subsequently, the expression level of MGAT2 is determined. The expression level of MGAT2 may be determined according to a method well-known to a person skilled in the art. For example, the mRNA of MGAT2 gene may be extracted in a conventional manner, and used as a template in the Northern hybridization method or RT-PCR method; thus, the transcription level of MGAT2 gene can be determined. Further, the expression level of MGAT2 gene can be determined using a DNA array technology.

The fraction containing MGAT2 coded by the MGAT2 gene may be recovered in a conventional manner, and the expression of MGAT2 is detected by electrophoresis such as SDS-PAGE; thus, the translation level of the gene can be determined It is also possible to carry out the Western blotting method using an antibody against MGAT2 to detect the expression of MGAT2; thus, the gene can be determined at the translation level. In this situation, there is no particular limitation in the antibody used in detection of MGAT2 as far as it is a detectable antibody, including monoclonal antibodies and polyclonal antibodies. The antibody may be prepared in a method well known to a person skilled in the art. Specifically, for example, a polyclonal antibody may be prepared as follows. Namely, a recombinant protein or its partial peptide which is expressed as MGAT2 or a fused protein of MGAT2 and GST in a microorganism such as *Escherichia coli* is immunized to rabbit etc. to yield serum. This may be purified, for example, by means of precipitation with ammonium sulfate, protein A column, protein G column, ion-exchange chromatography, MGAT2-coupled affinity column, and the like. For the monoclonal antibody, for example, MGAT2 or its partial peptide is immunized to a small animal such as mouse, from which is then removed the spleen; the latter is mashed to separate cells, and the cells are fused with murine myeloma cells using a reagent such as polyethylene glycol; from the resulting fused cells (hybridoma), a clone capable of producing an antibody binding MGAT2 may be selected. Then, the resulting hybridoma is transplanted intraperitoneally to mice, from which ascites is recovered; and the resulting monoclonal antibody may be purified, for example, by means of precipitation with ammonium sulfate, protein A column, protein G column, ion-exchange chromatography, MGAT2-coupled affinity column, and the like.

In the second embodiment, the test compound which makes the expression level of MGAT2 decrease or increase is selected compared with the case in which no test compound is contacted. The selected compounds contain a compound or compounds decreasing or increasing the expression of MGAT2; the compound decreasing the expression acts as an MGAT2 inhibitor and the compound increasing the expression acts as an MGAT2 enhancer. The MGAT2 inhibitor has an effect inhibiting the expression or activity of MGAT2, and enables to inhibit the synthesis of TG, i.e. inhibition of the synthesis/accumulation of fat; thus, it allows to obtain a compound effective in prevention or treatment of diseases caused by the excessive synthesis and accumulation of fat. On the other hand, the enhancer which enhances the MGAT2 activity as a result of comparison has an effect enhancing the expression or activity of MGAT2, and enables to normalize the lack and defect of the synthesized TG, i.e. synthetic insufficiency of fat; it allows to obtain a compound effective in prevention or treatment of diseases caused by the synthetic insufficiency of fat.

In the third embodiment of the screening method of compounds, the invention provides a method for screening a compound effective in prevention or treatment of diseases induced by abnormal lipid metabolism, which comprises a step for providing a cell or cell extract containing a DNA to which a reporter gene functionally ligates at downstream of the promoter region of DNA coding for MGAT2, a step for making a test compound contact with the cell or cell extract, a step for determining the expression level of the reporter gene in the cell or cell extract, and a step for selecting a test compound capable of decreasing or increasing the expression level of the reporter gene compared to the case of no contact with the test compound.

In the third embodiment, the term "functionally ligate" means that the promoter region of MGAT2 gene ligates to the reporter gene so that the ligating of the promoter region of MGAT2 gene to the transcription factor induces the expression of reporter gene. Accordingly, even if the reporter gene ligates to another gene to form a fusion protein with other gene product, as far as a transcription factor ligates to the promoter region of MGAT2 gene and induces the expression of the fused protein, such a case is encompassed in the term "functionally ligate". In this situation, there is no particularly limitation in the reporter gene, as far as its expression is detectable, including, for example, CAT gene, LacZ gene, luciferase gene, β-glucuronidase gene (GUS) and GFP gene. The above reporter gene includes DNA coding for MGAT2.

The cell or cell extract containing a DNA to which a reporter gene functionally ligates at downstream of the promoter region of DNA coding for MGAT2 may be prepared according to the method as mentioned in the first embodiment.

In the third embodiment, subsequently, the above cell or cell extract is allowed to contact with a test sample. In the invention, the "contact" may be carried out in the same manner as described in the second embodiment.

Subsequently, the expression level of the above reporter gene contained in the cell or cell extract is determined.

The expression level of the reporter gene may be determined depending on the variation of the reporter gene employed according to a method well known to a person skilled in the art. For example, when the reporter gene is a CAT gene, the expression level of the reporter gene can be determined by detecting acetylation of chloramphenicol with the relevant gene product. When the reporter gene is a LacZ gene, the expression level may be determined by detecting coloration of a pigment compound by the catalytic action of the relevant gene expression product. When the reporter gene is a luciferase gene, the expression level may be determined by detecting fluorescence of a fluorescent compound generated by the catalytic action of the relevant gene expression product. When the reporter gene is a β-glucuronidase gene, the expression level may be determined by detecting luminescence of glucuron or luminescence of 5-bromo-4-chloro-3-indolyl-β-glucuronide (X-Gluc) by the catalytic action of the relevant gene expression product. In addition, when the MGAT2 gene is per se a reporter gene, the expression level of the relevant gene may be determined according to the method as described in the second embodiment.

In the third embodiment, subsequently, a test compound which decreases or increases the expression level of the reporter gene is selected in comparison with the case in which the test compound is not contacted. The selected compounds contain a compound or compounds decreasing or increasing the expression of MGAT2; the compound decreasing the expression acts as an MGAT2 inhibitor and the compound increasing the expression acts as an MGAT2 enhancer. The MGAT2 inhibitor has an action inhibiting the expression or activity of MGAT2, and enables to inhibit the synthesis of TG, i.e. inhibition of the synthesis/accumulation of fat; thus, it allows to obtain a compound effective in prevention or treatment of diseases caused by the excessive synthesis and accumulation of fat. On the other hand, the enhancer which enhances the MGAT2 activity as a result of comparison has an action enhancing the expression or activity of MGAT2, and enables to normalize the lack and defect of the synthesized TG, i.e. synthetic insufficiency of fat; thus, it allows to obtain a compound effective in prevention or treatment of diseases caused by the synthetic insufficiency of fat.

Drugs for Prevention or Treatment of Diseases Induced by Abnormal Lipid Metabolism The drugs for prevention or treatment of diseases induced by abnormal lipid metabolism in the invention is characterized by containing as an active ingredient a compound capable of decreasing the expression or activity of MGAT2. The compounds obtained by the screening method for the compounds of the invention are also included in the drugs of the invention.

The drugs for prevention or treatment of the diseases induced by abnormal lipid metabolism include those containing as an active ingredient a compound capable of decreasing or enhancing the expression or activity of MGAT2. As for the compounds decreasing or enhancing the expression or activity of MGAT2, there is no limitation in varieties thereof as far as they act to decrease or enhance the expression or activity of MGAT2. Such compounds include, for example, naturally occurring compounds, organic compounds, inorganic compounds, proteins, antibodies, peptides, or nucleic acids. The relevant nucleic acid includes DNA and RNA, for example, antisense RNA and siRNA.

There is no particular limitation in the above antibodies, including polyclonal antibodies as well as monoclonal antibodies. In addition to anti-serum obtained from an immune animal such as rabbit by immunization with MGAT2, all classes of polyclonal antibodies and monoclonal antibodies, additionally human-type antibodies obtained by gene recombination and human antibodies are also included. The above antibodies may be prepared according to the following methods. For example, polyclonal antibodies may be prepared by immunizing a small animal such as rabbit with MGAT2 to obtain serum, which is applied to an MGAT2-coupled affinity column to obtain a fraction recognizing MGAT2 alone; then, this fraction is applied to a protein A or protein G column to yield immunoglobulin G or M. For the monoclonal antibody, MGAT2 is immunized to a small animal such as mouse, from which is then removed the spleen; the spleen is mashed to separate cells, and the cells are fused with murine myeloma cells using a reagent such as polyethylene glycol; from the resulting fused cells (hybridoma), a clone capable of producing an antibody against MGAT2 may be selected. Then, the resulting hybridoma is transplanted intraperitoneally to mice, from which ascites is recovered; and the resulting monoclonal antibody may be purified, for example, by means of precipitation with ammonium sulfate, protein A, protein G column, DEAE ion-exchange chromatography, MGAT2-coupled affinity column, and the like. The above antibodies can be used in purification or detection of MGAT2 and also used as drugs for controlling the function of MGAT2. When the antibody is used as a drug for human, a human antibody or humanized antibody is used effectively in view of immunogenicity. The human antibody or humanized antibody can be prepared according to a method well known to a person skilled in the art. For example, a human antibody may be prepared by immunizing a mouse, of which the immune system is replaced by the human immune system, with MGAT2. The humanized antibody may be prepared, for example, by cloning the antibody gene from a monoclonal antibody-producing cell and then grafting the antigen determinant site to the existing human antibody according to a CDR graft method.

The compound decreasing the expression of MGAT2 includes RNA complementary to the transcript of DNA coding for MGAT2 or ribozyme specifically cleaving the relevant transcript. DNA coding for MGAT2 includes DNA comprising the base sequence as described in SEQ ID NO: 1 (human) and 3 (mouse), DNA coding for a protein of the amino acid sequences as described in SEQ ID NO: 2 (human) and 4 (mouse), and a naturally occurring DNA coding for the protein comprising the amino acid sequence as described in SEQ ID NO: 2 or 4 in which one or two or more amino acids have been substituted, deleted, added and/or inserted.

One embodiment of "RNA complementary to the transcript of DNA coding for MGAT2" as mentioned above is an antisense RNA complementary to the transcript of DNA coding for MGAT2. As for the action of antisense nucleic acid inhibiting the expression of the target gene, the following factors exist: namely, inhibition of the initiation of transcription by triple strand formation, inhibition of transcription by hybrid formation with the site at which an open loop structure is generated locally by RNA polymerase, inhibition of transcription by hybrid formation with RNA on the way of synthesis, inhibition of splicing by hybrid formation at the juncture between an intron and an exon, inhibition of transfer from the nucleus to the cytoplasm by hybrid formation with mRNA, inhibition of splicing by hybrid formation with the capping site or poly A-adding site, inhibition of translation by hybrid formation with the binding site of translation-initiation factor, block of extension of the peptide chain by hybrid formation with the translation region or polysome-binding site of mRNA, and inhibition of the gene expression by hybrid formation with the interacting site between a nucleic acid and a protein. These inhibit the process of transcription, splicing or translation, to inhibit the expression of the target gene.

The antisense sequence used in the invention is able to inhibit the expression of the target gene by any one of the above actions. In one embodiment, when an antisense sequence complementary to the non-translation region proximal to the 5'-terminal of gene mRNA is designed, the inhibition of the translation of gene occurs effectively. On the other hand, a sequence complementary to the code region or the 3' non-translation region may be used. Thus, DNAs containing not only the antisense sequence of translation region of gene but also that of non-translation region are included in the antisense DNAs used in the invention. The antisense DNA to be used is ligated at the downstream of a proper promoter, preferably a sequence containing a transcription-terminating signal is ligated at 3'-side. Though such antisense DNA sequences are preferably complementary to the MGAT2 gene or a part thereof, as far as the expression of gene is inhibited effectively, it may not be complementary completely. The transcribed RNA has preferably 90% or more complementarity, more preferably 95% or more complementarity to the transcript of the target gene. In order to effectively inhibit the expression of the target gene using an antisense sequence, the length of the antisense DNA consists of at least 15 bases or more, preferably 100 bases or more, and more preferably 500 bases or more. Usually, the length of antisense DNA is shorter than 5 kb, preferably shorter than 2.5 kb.

When the compounds acting on MGAT2 of the invention is used as medicaments in humans and other animals, they may be administered per se as such and additionally as pharmaceutical preparations prepared in a well-known pharmaceutical method. For example, they may be used orally in a form of tablets (sugar coated if necessary), capsules, elixir, microcapsules, or alternatively parenterally in an injectable form of sterile solutions or suspensions with water or pharmaceutically acceptable other liquid. For example, it is considered that they are properly combined with pharmacologically acceptable carrier or medium, specifically, sterilized water or physiological saline, vegetable oil, emulsifying agent, suspending agent, surface activating agent, stabilizer, flavor, excipient, vehicle, anti-septic, binder, and the like, and formulated by mixing in a unit dose form required in generally recognized pharmaceutical practice.

The excipient miscible into tablets and capsules includes, for example, binders such as gelatin, corn starch, tragacanth gum, gum arabic; diluents such as crystalline cellulose; swelling agents such as corn starch, gelatin, alginic acid; lubricants such as magnesium stearate; sweeteners such as sucrose, lactose or saccharin; and flavors such as peppermint, akamono oil, or cherry. When the pharmaceutical unit form is capsule, a liquid carrier such as fat and oil may be added in addition to the above materials. The injectable sterile composition may be prescribed using a vehicle such as distilled water for injection according to a conventional pharmaceutical practice.

The injectable aqueous solution includes, for example, physiological saline, isotonic solution containing glucose or other adjuvant, such as D-sorbitol, D-mannose, D-mannitol, sodium chloride; a proper solubilizing agents, for example, alcohol, specifically, ethanol, polyalcohol, e.g., propylene glycol, polyethylene glycol, non-ionic surface activator, for example, Polysolvate 80 (TM), HCO-50 may be used together.

The oily solution includes sesame oil and soybean oil, and may be used together with a solubilizing agent such as benzyl benzoate or benzyl alcohol. In addition, a buffer, for example, phosphate buffer, sodium acetate buffer, soothing agent, for example, procaine hydrochloride, stabilizer, for example, benzyl alcohol, phenol, and anti-oxidant may be blended. Thus prepared injection solution is usually filled into proper ampoules.

Administration to a patient may be achieved by intra-arterial, intravenous, subcutaneous injection, and further nasally, intrabronchially, intramuscularly, percutaneously or orally according to a method well known in a person skilled in the art. The dosage is variable depending on the body weight or age of the patient or administration route, although it may properly be chosen by a person skilled in the art. In addition, it is also considered that if the relevant compound may be coded by DNA, the relevant DNA could be integrated in a vector for gene therapy to carry out the gene therapy. Though the dosage and the way of administration are variable depending on the body weight or age or condition, a person skilled in the art may properly choose them.

Though the dosage of the compound is diverse depending on the condition, the dose in oral administration is in general regarded as about 0.1 mg to 100 mg per day for an adult (body weight 60 kg), preferably about 1.0 to 50 mg, more preferably about 1.0 to 20 mg.

In the case of parenteral administration, though a dose is variable depending on the subject to be administered, target organ, condition, way of administration, etc., usually, it is considered advantageous that it may be administered intravenously in a form of injection at a dose of about 0.01 to 30 mg/day for an adult (body weight 60 kg), preferably about 0.1 to 20 mg, more preferably about 0.1 to 10 mg.

The disease which is a target of the administration of such a compound includes, for example, obesity, hyperlipemia (hypercholesterolemia, high LDL cholesterolemia, low HDL cholesterolemia, hypertriglyceridemia), hyperinsulinemia, arteriosclerosis, ischemic heart diseases (angina pectoris, myocardial infarction), stroke (cerebral hemorrhage, cerebral infarction), renal dysfunction (renal arteriosclerosis, renal failure), aberrant eye grounds (hemorrhage of the eye grounds, blindness), circulation disorder in limb (intermittent claudication, gangrene), an(hypo)β-lipoproteinemia, apoprotein B aberration, Anderson's disease, Tangier's disease, apo A-I deficiency (mutant), chronic hepatitis, hyperthyroidism, liver cirrhosis, hemolytic anemia, chronic pancreatitis, leukemia, malabsorption syndrome, malignant lymphoma, Addison's disease, chronic (acute) inflammation, malignant tumor, spleen tumor, infection, obesity, type 2 diabetes mellitus, chronic hepatitis, myeloproliferative disease, renal failure, malignant tumor, low nutrition, nephrotic syndrome, malabsorption syndrome, and the like.

Method for Detection of Diseases Induced by Abnormal Lipid Metabolism

The method for detection of diseases induced by abnormal lipid metabolism of the invention is characterized in that it comprises a step for determining the amount of the expression of MGAT2 gene. The invention provides a method for detection of diseases induced by abnormal lipid metabolism, which comprises a step for determining the amount of the expression of MGAT2 gene. The term "expression of MGAT2 gene" here includes not only the expression of mRNA of MGAT2 but also the expression of MGAT2. In the method for detection of the invention, when the expression of MGAT2 gene increases or decreases, there is a possibility of abnormal lipid metabolism, and thus it is judged there is a possibility of suffering from a disease caused by it.

The followings illustrate an embodiment of the detection method of the invention, but the invention is not limited thereby. In one embodiment of the above method for detection, first, an RNA sample is prepared from a subject. The RNA sample can be extracted from the blood, skin of the subject, tissue or cells removed by surgical operation.

In this method, subsequently, the amount of RNA coding for MGAT2 contained in the relevant RNA sample is determined Then, the amount of RNA determined is compared to that of the control. Such a method is exemplified by Northern blotting method, DNA array method, or RT-PCR method.

The above detection method may be carried out as mentioned below by determining the amount of expressed MGAT2. First, a polypeptide sample is prepared from a subject. The polypeptide sample may be prepared, for example, from the blood, skin, oral mucosa, hair of the subject, tissue or cells removed by surgical operation.

In this method, subsequently, the amount of MGAT2 contained in the relevant polypeptide sample is determined. Then, the amount of MGAT2 determined is compared to that of the control. Such a method is exemplified by SDS polyacrylamide electrophoresis, as well as Western blotting, dot blotting, immune precipitation, enzyme-linked immunosorbent assay (ELISA), and immunofluorescence, using an antibody capable of binding MGAT2.

The invention also provides a method for detection of diseases induced by abnormal lipid metabolism, which comprises a step of detecting a mutation in the gene region of MGAT2. In this method for detection, when a mutation occurs in the gene region of MGAT2, the expression amount of MGAT2 changes aberrantly, and thus in such a case it is judged there is an aberrance in lipid metabolism. In the invention, the gene region of MGAT2 means those influencing on the MGAT2 gene and its expression. There is no particular limitation in the region influencing on the expression of MGAT2 gene, including, for example, promoter region.

As for the mutation in the invention, there is no limitation in its type, its number and its site, as far as its mutation causes the abnormal growth or abnormal differentiation of cells. The type of the above mutation includes, for example, mutation by deletion, substitution, or insertion.

The followings describe a preferred embodiment of a detection method which comprises a step for detection of mutation generated in the gene region of MGAT2, but the method of the invention is not limited thereto.

In a preferred embodiment of the above detection method, first, a DNA sample is prepared from a subject. The DNA sample can be prepared based on the chromosome DNA, or RNA extracted from the blood, skin, oral mucosa, hair of the subject, tissue or cells removed by surgical operation.

In this method, subsequently, the DNA containing the gene region of MGAT2 is isolated. The isolation of the gene region of MGAT2 may be carried out, for example, by means of PCR etc. with chromosomal DNA or RNA as a template, using a primer which hybridizes to DNA containing the relevant gene region.

In this method, subsequently, the base sequence of the isolated DNA is determined. The determination of the base sequence of the isolated DNA may be achieved according to a method well known to a person skilled in the art.

In this method, subsequently, the determined base sequence of DNA is compared to that of the control. In this invention, the control is referred to DNA containing the gene region of a normal (wild type) MGAT2. In general, the DNA sequence containing the region of MGAT2 gene of a healthy person is considered to be normal; thus, the above term "compare to that of the control" usually means the comparison to the DNA sequence containing the region of MGAT2 gene of a healthy person.

Detection of the mutation in the invention may be carried out according to the following method. First, a DNA sample is prepared from a subject. Subsequently, the DNA sample thus prepared is cleaved with a restriction enzyme. Then, the DNA fragments are separated according to the size. Then, the size of DNA fragment thus detected is compared to the control. In another embodiment, first, a DNA sample is prepared from a subject. Subsequently, DNA containing the region of MGAT2 gene is amplified. Further, the amplified DNA is cleaved with a restriction enzyme. Then, the DNA fragments are separated according to the size. Then, the size of DNA fragment thus detected is compared to the control.

Such methods include, for example, a method utilizing restriction fragment length polymorphism (RFLP) or PCR-RFLP. Specifically, when a mutation exists at the recognition site of restriction enzyme, or when a base insertion or deletion exists in the DNA fragment produced by treatment with a restriction enzyme, the size of the fragment produced after treatment with the restriction enzyme is varied compared to the control. This portion containing the mutation is amplified by means of PCR, and treated with respective restriction enzymes; these mutations can be detected by electrophoresis as the difference of mobility of each band. Alternatively, a chromosomal DNA is treated with these restriction enzymes, and after electrophoresis, the presence or absence of the mutation can be detected by Southern blotting using a probe DNA of the invention. The restriction enzyme applicable may properly be selected according to the respective mutations. In this method, in addition to the genomic DNA, RNA prepared from a subject is treated with a reverse transcription enzyme to yield cDNA, which can be cleaved directly with a restriction enzyme and subjected to Southern blotting. Further, this cDNA is used as a template in PCR to amplify the DNA containing the region of MGAT2 gene, which can be cleaved with restriction enzymes to check for the difference of mobility.

In an alternative method, first, a DNA sample is prepared from a subject. Next, DNA containing the gene region of MGAT2 is amplified. Further, the amplified DNA is dissociated to single-strand DNAs. Then, the dissociated single-strand DNAs are separated on a native gel. The mobility of the separated single-strand DNA on the gel is compared to that of the control. Such a method includes, for example, PCR-SSCP (single-strand conformation polymorphism). This method has such advantages that the operation is relatively simple and can be made in a small amount of the sample to be tested; thus, it is particularly preferred in screening of a large number of DNA samples. The fundamental principle is as follows. When a double-strand DNA fragment is dissociated into single-strands, each strand forms independent higher-order structure dependent on its base sequence. When this dissociated DNA strands are applied to electrophoresis on polyacrylamide gel containing no denaturant, the single-strand DNAs, which are complementary each other and have the same strand length, move to positions different from each other according to the difference of respective higher-order structure. Even only one base substitution makes this single-strand higher-order structure change and shows different mobility in polyacrylamide gel electrophoresis. Detection of this change of the mobility, accordingly, leads to detection of the presence of mutation induced by point mutation, deletion, or insertion in the DNA fragments.

Specifically, first, DNA containing the gene region of MGAT2 is amplified by means of PCR etc. In general, the extent to be amplified is preferably approximately 200-400 bp. In carrying out PCR, the reaction condition may be chosen properly by a person skilled in the art. In PCR, it is possible to label the amplified DNA product by using a primer labeled with an isotope such as $^{32}P$, fluorescent pigment, or biotin. Alternatively, PCR may be carried out by adding a substrate base labeled with an isotope such as $^{32}P$, fluorescent pigment, or biotin to the PCR reaction mixture to label the amplified DNA product. In addition, the labeling may be conducted by adding a substrate base labeled with an isotope such as $^{32}P$, fluorescent pigment, or biotin to the amplified DNA fragment using the Klenow enzyme after PCR reaction. Thus resulting labeled DNA fragment is heated to denature and applied to electrophoresis on polyacrylamide gel containing no denaturant such as urea. In this situation, the addition of a proper amount (about 5-10%) of glycerol to polyacrylamide gel enables to improve the condition for separation of the DNA fragments. Electrophoresis is usually conducted under a condition at room temperature (20-25° C.), though it is variable depending on the nature of each DNA fragment, and when no preferable separation is achieved, the temperature at which the best mobility is attained has to be searched within a temperature of 4-30° C. After electrophoresis, the mobility of DNA fragments is detected and analyzed by means of autoradiography with a X-ray film or a fluorescence-detecting scanner. When the bands detected have difference in their mobility, these bands can be cut out directly from the gel, amplified again by PCR, and directly sequenced to confirm the presence of mutation. When no labeled DNA is used, the bands on the gel after electrophoresis can be detected by staining with ethidium bromide or silver stain.

In an alternative method, first, a DNA sample is prepared from a subject. Subsequently, DNA containing the gene region of MGAT2 is amplified. Further, the amplified DNA is separated on gel in which the concentration of DNA denaturant is gradually increased. Then, the mobility of the separated DNA on gel is compared to that of the control. Such a method is exemplified, for example, by denaturant gradient gel electrophoresis: DGGE). DGGE method may be carried out by migrating a mixture of DNA fragments on polyacrylamide gel in which a denaturant has a gradient in the concentration to separate the DNA fragments based on their difference in unstability. When the unstable DNA fragment having a mismatch moves up to the portion of a certain concentration of a denaturant in gel, the DNA sequence around the mismatch dissociates partially because of its unstability to give a single strand. The migration of the partially dissociated DNA fragment becomes very slow and generates difference from the mobility of the non-dissociated complete double-strand DNA; thus, both can be separated. Specifically, DNA containing the region of MGAT2 gene is amplified by PCR or the like using a primer or the like of the invention, applied to electrophoresis on polyacrylamide gel in which the concentration of a denaturant such as urea gradually increases along with the migration, and compared to the control. When there is a mutation in the DNA fragment, the DNA fragment yields single-strands at the position lower in the concentration of the denaturant, and the migration rate becomes extremely slow; the detection of the difference of mobility enables to detect the presence or absence of mutation.

Further in another method, first, DNA containing the region of MGAT2 gene prepared from a subject and a substrate (plate) on which a nucleotide probe hybridizing the relevant DNA is immobilized, are provided. The term "substrate (plate)" in the invention means a plate-type material on which a nucleotide probe can be immobilized. In the invention, the nucleotide includes oligonucleotides and polynucleotides. There is no particular limitation in the substrate (plate) used in the invention, as far as a nucleotide probe can be immobilized thereon, and the substrate (plate) generally used in a DNA array technology can preferably be used. In general, a DNA array is composed of many thousands of nucleotides printed on a substrate in high density. Usually, these DNAs are printed on the surface layer of a non-permeable (non-porous) substrate (plate). The surface layer of the substrate is generally of glass, but a permeable (porous) membrane, for example, nitrocellulose membrane may also be used.

In a method for immobilization (array) of nucleotides of the invention, an array based on oligonucleotides made by Affymetrix & Co. is exemplified. In the array of oligonucleotides, the oligonucleotides are usually synthesized in situ. For example, in situ synthetic methods for oligonucleotides, such as a photolithographic technology (Affymetrix & Co.) and an ink jet technology (Rosetta Inpharmatics Co.) for immobilizing a chemical substance, have already been known; all of these technologies can be employed in preparation of the substrates (plates) of the invention.

There is no particular limitation in the nucleotide probes to be immobilized on a substrate (plate), as far as the mutation of the region of MGAT2 gene can be detected. Namely, the relevant probe includes those which are able to hybridize to DNA containing the region of MGAT2 gene. As far as specific hybridization is possible, it is not necessary to be completely complementary to DNA containing the relevant gene region. In the invention, the length of nucleotide probe binding to the substrate is usually 10-100 bp, preferably 10-50 bp, more preferably 15-25 bp in the case of immobilization of oligonucleotides.

In the invention, subsequently, DNA containing the region of MGAT2 gene is allowed to contact with a substrate (plate). During this process, DNA is allowed to hybridize to the above nucleotide probe. Though the reaction solution and the reaction condition for hybridization are variable depending on a variety of factors such as the length of nucleotide probe to be immobilized on a substrate, in general, the hybridization may be achieved according to a method well known in a person skilled in the art.

In the invention, subsequently, the strength of hybridization between DNA containing the region of MGAT2 gene and the nucleotide probe immobilized on the substrate is detected. Detection may be carried out, for example, by reading out a fluorescent signal by a scanner etc. In the DNA array, the DNA immobilized on a slide glass is generally called probe; on the other hand, the DNA labeled in a solution is called target. Thus, the above nucleotide immobilized on a substrate is described herein as nucleotide probe. In the invention, further, the strength of hybridization detected is compared to the control.

In addition to the above method, in order to detect only a mutation at a certain position, an allele specific oligo nucleotide (ASO) hybridization method may be utilized. An oligonucleotide containing a base sequence in which a mutation is considered to exist is prepared, and this is hybridized with DNA; thus, when there is a mutation, the efficiency of hybridization is decreased. This can be detected by means of Southern blotting, or a method utilizing a property in which a special fluorescent reagent is intercalated in the gap of hybrid to quench.

In addition, in the invention, a MALDI-TOF/MS method, TaqMan PCR method, Invader method, Pyrosequencing method, AcycloPrime method, SNuPE method, and the like may also be employed.

When the result of detection according to the method for detection in the invention indicates an increase of the expression of MGAT2 in comparison with the normal tissue or normal cell, or a rise of the MGAT2 activity in comparison with the normal tissue or normal cell, then diagnosis is made to be a disease caused by excessive lipid such as obesity, hyperlipemia (hypercholesterolemia, high LDL cholesterolemia, low HDL cholesterolemia, hypertriglyceridemia), hyperinsulinemia, type 2 diabetes mellitus, or arteriosclerosis. On the other hand, when the expression of MGAT2 is reduced in comparison with the normal tissue or normal cell, or the MGAT2 activity is decreased in comparison with the normal tissue or normal cell, then diagnosis is made to be a disease caused by lipid deficiency such as an(hypo)β-lipoproteinemia, apoprotein B aberration, Anderson's disease, Tangier's disease, apo A-I deficiency (mutant), chronic hepatitis, or hyperthyroidism.

WORKING EXAMPLES

The invention will be more specifically explained by the following examples, which are not intended as limitation thereof.

Example 1

Preparation of MGAT2-Deficiency Mice

In order to investigate the physiological function of MGAT2 in vivo, a MGAT2-deficiency mice were prepared according to the following procedure.

Murine MGAT2 comprises 6 exons. As shown in FIG. 1, a targeting vector was designed, wherein the region containing Exons 3, 4 and 5 were put between the loxP sequences so that they can be eliminated conditionally with the cre enzyme activity. The 5'-side arm (2.5 kb) and the site (1.6 kb) containing Exons 3, 4 and 5 were prepared by amplification by PCR using murine BAC clone (Invitrogen Co.) as template.

The base sequences of primers for PCR used here in preparation of the 5'-side arm are as follows.

```
SAF2Mlu:
                                        (SEQ ID NO: 5)
5'-ACGCGTGAGGGAAAGTCTTTCTGAGGCATCTCCTC-3'

SAR1Mlu:
                                        (SEQ ID NO: 6)
5'-ACGCGTCCACAGAGATGGGTGCTGTGTGGGACAGTGGG-3'
```

The base sequences of primers for PCR used in preparation of the arm containing Exons 3, 4 and 5 are as follows.

```
LTF1Mro:
                                        (SEQ ID NO: 7)
5'-TCCGGAATACTCAGGATTATGAACATCTTGAGACTCAGAGGC-3'

LTR1Mro:
                                        (SEQ ID NO: 8)
5'-TCCGGATCTCCGCTCACCTATGGTGGTGATGGGC-3'
```

In order to make the loxP site adjacent to the site containing Exons 3, 4 and 5, first the nucleic acid fragment (1.6 kb) containing Exons 3, 4 and 5 obtained by PCR was subcloned to the SmaI site of modified ploxP30NeopA (Kurabo Industries). Then, this plasmid was treated with XhoI, and the resulting nucleic acid fragment was introduced into the SalI site of the targeting vector.

The nucleic acid fragment (2.5 kb) of the 5' side obtained by PCR was introduced into the MluI site of the targeting vector.

Further, in order to prepare an arm of the 3' side, among the nucleic acid fragments (containing Exon 6) derived from 12 kb BAC treated with XhoI, the XhoI-MluI nucleic acid fragment (3.5 kb) was substituted with the above 1.6 kb nucleic acid fragment. The nucleic acid sequences of primers for PCR used here in cloning of 1.6 kb nucleic acid fragment are as follows.

```
LAF2MluBgl:
                                        (SEQ ID NO: 9)
5'-ACGCGTAGATCTGGATCAGGAATAGGGCCTGAGCTAGATGC-3'

LAR2:
                                        (SEQ ID NO: 10)
5'-AGGTAGAAGCAGTACTCGGTTCACACATCACC-3'
```

Thus resulting 8.9 kb nucleic acid fragment of the 3' side was treated with BglII, and introduced into the BglII site of the targeting vector.

The resulting targeting vector was linearized by treatment with NotI and introduced in v6.5ES cell by means of electroporation.

Subsequently, in order to identify a homologous recombinant, the ES cell showing neomycin resistance was screened, and the clone in which the generation of homologous recombination was confirmed was selected by means of PCR. Next, the homologous recombinant ES cell clone was injected into C57BL/6J blastocyst and transplanted to a pseudo-pregnant mouse. Chimera male mouse was mated with a C57BL/6N mouse, and thus a mouse showing the transfer to a germ cell line was obtained.

In order to obtain a Mgat2 knock-out mouse (−/−), TgEIIa-cre transgenic mice (Jackson Laboratories) were mated with Mgat2 lox (ex 3, 4, 5)/lox (ex 3, 4, 5) mice. The mice all were bred under a standard condition of light/dark cycles of 12 hours, during which breeding a standard pellet chow CE-2 (Krea Co.) for rodents was given properly.

Example 2

Expression of MGAT2 in MGAT2 Deficiency Mice

In order to confirm the expression of mRNA and a protein of MGAT2 in the small intestine and adipose tissue of MGAT2 deficiency mice, the following test was carried out.

mRNA was prepared from the small intestine mucosa and adipose tissue using a RNeasy kit (Qiagen), and after synthesis of cDNA with Superscript III (Invitrogen), it was determined by means of a TaqMan PCR method using the following probes.

```
TaqMan probe:  CCATCACCACCATAGTG    (SEQ ID NO: 11)

FW primer:     CATGCCCTTCCGCCAG     (SEQ ID NO: 12)

RV primer:     ATCTGCACCTCGATGGGCT  (SEQ ID NO: 13)
```

FIG. 2 shows the result of investigation for the expression of MGAT2 mRNA in the small intestine of MGAT2 deficiency mice, and FIG. 3 shows the result of investigation for the expression of mRNA in the adipose tissue of MGAT2 deficiency mice. All of the results were represented by the means±standard error (SE) of the data in respective wild-type, heterozygous and homozygous mice (n=5). In the MGAT2 homo-deficiency mice, the expression of MGAT2 mRNA disappeared almost completely in both of the small intestine and adipose tissue. On the other hand, in the MGAT2 hetero-deficiency mice, the degree of expression was medium, that is, 60% in the small intestine compared to the wild type, and 19% in the adipose tissue compared to the wild type. These data respectively show a significant difference; namely, FIG. 2 shows the significant difference (p<0.001) for the wild type mice, and FIG. 3 shows the significant difference (homo: p<0.001; hetero: p<0.05) for the wild type mice.

In addition, in order to confirm the expression of proteins in the MGAT2 deficiency mice, the following test was carried out.

First, the membrane fraction of the small intestine and adipose tissue was separated by means of SDS polyacrylamide gel electrophoresis and transcribed on a PVDF membrane to prepare a sample for Western blotting. The antibody used in Western blotting was prepared by immunizing a rabbit with a peptide (IIVGGAQEALDARPG: SEQ ID NO:14) corresponding to a part of murine MGAT2, followed by processing in a conventional manner to yield an anti-mouse MGAT2 rabbit polyclonal antibody. The above PVDF membrane and anti-mouse MGAT2 antibody were used in Western blotting, where the detected bands were determined with a LAS3000 luminoimage analyzer.

As shown in FIG. 4, the expression of MGAT2 protein in the MGAT2 deficiency mice also disappeared completely in the small intestine. In addition, the expression of MGAT2 protein similarly almost disappeared in the adipose tissue. The bands detected by Western blotting were determined with a LAS3000 luminoimage analyzer; as a result, as shown in FIG. 5, the expression of MGAT2 was approximately ½ of that of the wild type in the small intestine of the MGAT2 hetero-deficiency mice (p<0.001, n=5).

From the above results, it was confirmed in the MGAT2 deficiency mice that the expression of MGAT2 in the homo-deficiency mice was inhibited completely at the mRNA and protein level. In the hetero-deficiency mice, the degree of the expression of MGAT2 was approximately the mid-point between the homo-deficiency mice and the wild type mice, and it was confirmed that an expected gene-deficiency mouse was obtained by targeting of the MGAT2 gene.

Example 3

Activity of MGAT2 in the MGAT2-Deficiency Mice

In order to confirm the activity of MGAT2 in the MGAT2-deficiency mice, the MGAT activity of the microsomal fraction in the small intestine mucosa was investigated according to the following procedure.

First, the microsomal fraction in the small intestine mucosa was added to a reaction mixture of 100 mM Tris-HCl (pH7.5), 200 mM sucrose, 5 mM $MgCl_2$, 1 mg/ml BSA, 200 μM monoolein/1000 μM phosphatidylcholine, 25 μM [14]-oleoyl-CoA so that the total volume became 100 μl, and incubated at 37° C. for 20 minutes to make the enzyme reaction proceed. Thereafter, 100 μl of 2-propanol/heptane/water (80/20/2) was added to the reaction mixture to terminate the reaction. Additionally, 200 μl of heptane was added, then stirred and centrifuged; the heptane layer was applied to thin layer chromatography (silica gel 60; Merck & Co.) for separation. The diglyceride and triglyceride fractions obtained by thin layer chromatography respectively were measured for the radioactivity as the MGAT activity.

As shown in FIG. 6, the MGAT activity in the small intestine was decreased to about 5% in the MGAT2-deficiency mice compared to the wild type, and it was 70% in the MGAT2 hetero-deficiency mice compared to WT ($p<0.001$, n=5).

From the above results, it was confirmed in the MGAT2 deficiency mice that the MGAT2 activity in the small intestine in the homo-deficiency mice was inhibited almost completely. In the hetero-deficiency mice, the activity of MGAT was approximately the mid-point between the homo deficiency mice and the wild type mice, and it was confirmed that an expected gene-deficiency mice were obtained by targeting of the MGAT2 gene.

Example 4

Analysis of the General Conditions in the MGAT2 Deficiency Mice

In order to investigate the physiological function of MGAT2 in vivo, the phenotype of the MGAT2 deficiency mice was analyzed.

First, the MGAT2 deficiency mice including the heterozygote and homozygote mice all were viable. In addition, the generic condition of the MGAT2 deficiency mice was observed and the spontaneous kinetic momentum was measured. The condition and items to be studied are as follows.

The wild type mice, MGAT2 hetero-deficiency mice, and MGAT2 homo-deficiency mice which were 9-11 weeks of age, were used in N=8 for male and female respectively (N=5 for female homo only).
Body Weight:
Male: Wild type: 27.3±0.4 g; hetero: 27.0±0.2 g; homo: 25.9±0.9 g
Female: Wild type: 21.9±0.9 g; hetero: 21.6±0.4 g; homo: 21.6±0.6 g Observed Item:
Central nervous condition (stereotype, grooming, aggressiveness, vocalization)
Central excitation (raising of tail, tremor, convulsion)
Moving function (searching motion, staggering gait, pose, surprise/sense of touch/algesia reaction)
Muscular tension (grasping power, body tension)
Reflex (corneal reflex, body righting reflex)
Autonomic nervous condition (piloerection, agony reaction, choroid fissure, exopthalmos, skin color, respiration rate, urination, defecation, lacrimation, salivation, body temperature)
Others (appearance, lie of hair, body weight, etc.)
Spontaneous Kinetic momentum
Total activity during the measured period (7 days)
Circadian rhythm of the activity keeping in phase with light and dark cycle
Habituation pattern in a new environment 4 hours after the starting of measurement As a result of the above observation, no difference between the wild type mice, MGAT2 hetero-deficiency mice and MGAT2 homo-deficiency mice was observed. In addition, no difference in the histopathological analysis was recognized, too.

Example 5

Analysis of Absorption of Neutral Fat (TG) in MGAT2 Deficiency Mice

Since MGAT2 is considered to be involved in absorption of fat in the small intestine, the absorption of neutral fat in the MGAT2 deficiency mouse was investigated.

First, the male MGAT2 homo-deficiency mice, hetero-deficiency mice and wild-type mice of 11-12 weeks of age were fasted for 16 hours, to which were then administered orally 10 ml/kg of corn oil. One, two and three hours after administration, the blood was collected from the tail vein, and the plasma TG was determined with a Determiner L TG II kit (Kyowa Medex).

As shown in FIG. 7 and FIG. 8, the increase of plasma TG after administration of corn oil was inhibited by about 79% in the MGAT2 deficiency mice ($p<0.05$, n=5-8). On the other hand, no noticeable change was observed in the MGAT2 hetero-deficiency mice. From these results, it was suggested that MGAT2 is involved in the absorption of lipid in the small intestine, and a MGAT2 inhibitor could have an effect of inhibiting the absorption of lipid.

Example 6

Analyses of Body Weight, Body Fat Rate and Food Consumption in the MGAT2 Deficiency Mice In order to investigate the influence of MGAT2 on the body weight, the weight of the MGAT2 deficiency mice was measured.

Using male MGAT2 homo-deficiency mice and wild type mice of 13-14 weeks of age, the body weight was compared. The weight of the MGAT2 homo-deficiency mice was reduced by 8% significantly compared to that of the wild type mice.

For the same mice, the body fat rate was determined by means of NMR (Minispec Analyzer; Bruker Co.); the body fat rate in the MGAT2 homo-deficiency mice was observed to decrease by 30% significantly compared to that of the wild type mice. However, no change in the weight rate from which the fat weight was subtracted was observed, indicating definitely that the decrease of the body weight in the MGAT2 homo-deficiency mice was due to reduction of body fat. In the MGAT2 hetero-deficiency mice, however, no change was observed both in the body weight and in the body fat rate compared to the wild type mice.

The food consumption in the MGAT2 homo-deficiency mice and wild type mice was also measured; no difference was observed between them.

From the above results, it was elucidated that the decrease of the body weight and body fat observed in the MGAT2 homo-deficiency mice was not due to inhibition of food consumption, but a phenomenon caused by abnormal lipid metabolism in vivo due to the deficiency of MGAT2.

Example 7

Analysis of Blood Parameters in the MGAT2 Deficiency Mice

In order to investigate the influence of MGAT2 on a variety of blood parameters, the following items were measured for the male MGAT2 deficiency mice and wild type mice of 17-18 weeks of age. The parentheses indicate the kits employed.
Plasma glucose (Determiner GL E kit; Kyowa Medex)
Plasma TG (Determiner L TG II kit; Kyowa Medex)
Total cholesterol (Determiner L TC kit; Kyowa Medex)
Free fatty acid (NEFA-HA TEST WAKO; Wako Pure Chemicals)

As a result, in the MGAT2 homo-deficiency mice, the plasma TG was significantly decreased by 52%, total cholesterol by 29%, and plasma glucose by 20%, respectively, compared to those of the wild type. In addition, there is a tendency of decrease of 27% in blood free fatty acids and 36% in hepatic TG.

In the above results, the MGAT2 deficiency mice showed not only decrease of the body weight and body fat but also decrease of the blood sugar, blood TG and blood cholesterol. Namely, it was found that MGAT2 plays an important role in control of lipid metabolism in vivo, and the deficiency of MGAT2 leads to inhibition of the synthesis of TG. This indicates that not only inhibition of MGAT2 is useful in improvement of the metabolic syndrome such as obesity, diabetes mellitus, hyperlipemia, fatty liver, but also enhancement of the function of MGAT2 is useful in treatment of diseases caused by lower fat, etc.

Example 8

Analysis of the Phenotype of the MGAT2 Deficiency Mice Loaded with High Fat Feed Subsequently, high fat feed containing 60% fat was loaded to MGAT2 homo-deficiency mice and wild type mice, and their phenotype was analyzed.

The body weight 4 weeks after loading of high fat feed was decreased by 20% significantly in the MGAT2 homo-deficiency mice compared to the wild type mice. The amount of body fat was measure by means of NMR, which indicated that the amount of body fat 4 weeks after loading of high fat feed was decreased by 52% significantly in the MGAT2 homo-deficiency mice compared to the wild type mice, indicating clearly the resistance against obesity induced by high fat feed.

On the other hand, no change in the body weight containing no fat was observed, and thus it was considered that the decrease of the body weight observed in the MGAT2 homo-deficiency mice was due to decrease of the body fat. In the MGAT2 hetero-deficiency mice, no significant difference was recognized in the body weight and amount of body fat compared to the wild type mice.

Subsequently, the blood parameters were measured in the MGAT2 homo-deficiency mice and wild type mice loaded with high fat feed. As a result, in the MGAT2 homo-deficiency mice to which high fat feed was loaded for 4 weeks, the total cholesterol and insulin value were significantly decreased by 38% and 61%, respectively, compared to the wild type mice, and the neutral fat and free fatty acid, respectively, showed a tendency of decrease of 44% and 18%.

Further, the amount of neutral fat in the liver and in the mucosa of small intestine after loading of high fat feed for 6 weeks was determined, resulting in significant decrease of 58% and 59%, respectively, in the MGAT2 homo-deficiency mice compared to the wild type mice.

From these results, it was shown that since the MGAT2 homo-deficiency mice exhibit tolerance to high-fat-feed derived obesity, hyperlipemia, hyperinsulinemia, type 2 diabetes mellitus, and fat liver, indicating that an MGAT2 inhibitor is effective in treatment of these diseases.

INDUSTRIAL APPLICABILITY

As described above, the gene-modified non-human mammal of the invention is useful as a model animal in diseases induced by aberrance of the route of lipid metabolism, particularly by abnormal synthetic route for TG, and can be utilized in screening of a drug for prevention or treatment of the relevant diseases. Further, it was elucidated from the above findings that an MGAT2 inhibitor and enhancer are effective for diseases induced by abnormal lipid metabolism. Namely, the invention provides a method for screening an MGAT2 inhibitor and enhancer by using the activity or expression of MGAT2 as indicator. In addition, since the expression and activity of MGAT2 are indicators for diseases induced by abnormal lipid metabolism, the use of the expression or activity of MGAT2 as indicator enables to detect the relevant diseases.

BRIEF DESCRIPTION OF DRAWINGS

FIG. 1 shows the structures of the targeting vectors which were used in preparation of an MGAT2 deficiency mouse.

FIG. 2 shows the comparative results of the expression of MGAT2 mRNA in the small intestine of an MGAT2 homo-deficiency mouse, MGAT2 hetero-deficiency mouse and wild type mouse.

FIG. 3 shows the comparative results of the expression of MGAT2 mRNA in the adipose tissue of an MGAT2 homo-deficiency mouse, MGAT2 hetero-deficiency mouse and wild type mouse.

FIG. 4 shows the comparative results by Western blotting for the expression of an MGAT2 protein in the small intestine of an MGAT2 homo-deficiency mouse, MGAT2 hetero-deficiency mouse and wild type mouse.

FIG. 5 shows the comparative results of the expression of an MGAT2 protein in the small intestine of an MGAT2 homo-deficiency mouse, MGAT2 hetero-deficiency mouse and wild type mouse.

FIG. 6 shows the results of comparison of the MGAT2 activity in the small intestine of an MGAT2 homo-deficiency mouse, MGAT2 hetero-deficiency mouse and wild type mouse.

FIG. 7 shows the results of time-dependent comparison of the change of plasma TG by administration of corn oil to an MGAT2 homo-deficiency mouse, MGAT2 hetero-deficiency mouse and wild type mouse. In Figs., the symbol ■ indicates the result in the wild type mouse, ▲ indicates the result in the MGAT2 hetero-deficiency mouse, and ▼ indicates the result in the MGAT2 homo-deficiency mouse.

FIG. 8 shows the results of comparison of the amount of plasma TG on administration of corn oil to an MGAT2 homo-deficiency mouse, MGAT2 hetero-deficiency mouse and wild type mouse.

The invention claimed is:

1. A transgenic mouse whose genome comprises a homozygous functional disruption of the monoacylglycerol acyltransferase (MGAT2) gene, which mouse exhibits, relative to a wild type mouse, a phenotype that is characterized by a decrease in body fat.

2. The mouse of claim 1, wherein an extraneous gene has been introduced into one or both of a pair of monoacylglycerol acyltransferase genes.

3. The mouse of claim 2, wherein the extraneous gene is a neomycin-resistant gene (neo) put between the loxP sequences or frt sequences.

4. The mouse of claim 1 which exhibits, relative to a wild type mouse, a phenotype that is also characterized by a decrease in body fat, blood triglyceride and blood cholesterol.

* * * * *